US010533018B2

(12) United States Patent
Franz et al.

(10) Patent No.: US 10,533,018 B2
(45) Date of Patent: Jan. 14, 2020

(54) ANTIMICROBIAL PROCHELATORS TO TARGET DRUG-RESISTANT BACTERIA AND METHODS OF MAKING AND USING THE SAME

(71) Applicant: Duke University, Durham, NC (US)

(72) Inventors: Katherine J. Franz, Durham, NC (US); David M. Besse, Durham, NC (US); Patrick C. Seed, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/740,910

(22) PCT Filed: Jun. 28, 2016

(86) PCT No.: PCT/US2016/039883
§ 371 (c)(1),
(2) Date: Dec. 29, 2017

(87) PCT Pub. No.: WO2017/004077
PCT Pub. Date: Jan. 5, 2017

(65) Prior Publication Data
US 2018/0194778 A1 Jul. 12, 2018

Related U.S. Application Data

(60) Provisional application No. 62/185,922, filed on Jun. 29, 2015.

(51) Int. Cl.
*C07D 501/52* (2006.01)
*A61P 31/04* (2006.01)

(52) U.S. Cl.
CPC .......... *C07D 501/52* (2013.01); *A61P 31/04* (2018.01)

(58) Field of Classification Search
CPC .................................................. C07D 501/52
USPC .......................................... 540/225; 514/203
See application file for complete search history.

(56) References Cited

U.S. PATENT DOCUMENTS

| 3,637,678 | A | 1/1972 | Webber et al. |
| 3,890,309 | A | 6/1975 | Ochiai et al. |
| 4,148,996 | A | 4/1979 | Palamidessi et al. |
| 5,187,172 | A | 2/1993 | Austin |
| 8,680,077 | B2 | 3/2014 | Franz et al. |
| 9,333,213 | B2 | 5/2016 | Franz et al. |
| 9,526,740 | B2 | 12/2016 | Franz et al. |
| 2014/0274955 | A1 | 9/2014 | Franz et al. |
| 2017/0224712 | A1 | 8/2017 | Franz et al. |

FOREIGN PATENT DOCUMENTS

WO 9202521 A1 2/1992

OTHER PUBLICATIONS

Banker et al., Prodrugs, Modern Pharmaceutics, 3rd edition, Revised and Expanded, pp. 451 and 596.*
Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1996.*
Bundgaard, Design of Prodrugs, Chapter 1, p. 1, 1985.*
Silverman, Prodrugs and Drug Delivery Systems, The Organic Chemistry of Drug Design and Drug action, Chapter 8, pp. 352-400, 1992.*
Greenwood, D. et al. "Dual-Action Cephalosporin Utilizing a Novel Therapeutic Principle." Antimicrobial Agents and Chemotherapy. American Society for Microbiology. Aug. 1976. vol. 10, No. 2. pp. 249-252.
O'Callaghan, Cynthia H. et al. "A New Cephalosporin with a Dual Mode of Action." Antimicrobial Agents and Chemotherapy. American Society for Microbiology. Aug. 1976. vol. 10, No. 2. pp. 245-248.
Besse, David M. et al. "Design of Antibacterial Prochelators to Target Drug-Resistant Bacteria". Ph.D. Thesis, Duke University, Department of Chemistry, Durham, NC. Mar. 24, 2016.
Wang, Qin et al. Stimulus-Responsive Prochelators for Manipulating Cellular Metals. Accounts of Chemical Research. Oct. 17, 2016. vol. 49, pp. 2468-2477.
International Search Report and Written Opinion issued in counterpart PCT Application No. PCT/US2016/039883 dated Oct. 4, 2016 (eight (8) pages).
O'Callaghan et al. 'A New Cephalosporin with a Dual Mode of Action', Antimicrobial Agents and Chemoterapy, 1976, vol. 10, No. 2, pp. 245-248. p. 246, Fig 1; col. 1, para 5; Table 1; Pi:J 246, col. 2, para 2.
International Preliminary Report on Patentability issued in counterpart PCT Application No. PCT/US2016/039883 dated Jan. 2, 2018 (six (6) pages).

\* cited by examiner

*Primary Examiner* — Patricia L Morris
(74) *Attorney, Agent, or Firm* — Olive Law Group, PLLC; Nathan P. Letts

(57) ABSTRACT

The present disclosure provides antibacterial prodrugs and methods of making and using the same.

9 Claims, 13 Drawing Sheets

Cellular metal concentrations of +Bla K-12 *E. coli*.

Concentration of DB4 -162 present by LC-MS after incubation with β-lactamase.

ANTIMICROBIAL PROCHELATORS TO TARGET DRUG-RESISTANT BACTERIA AND METHODS OF MAKING AND USING THE SAME

CROSS REFERENCE TO RELATED APPLICATIONS

This application is a § 371 national stage patent application, which claims priority to PCT International Patent Application No. PCT/US2016/039883, filed Jun. 28, 2016, and titled ANTIMICROBIAL PROCHELATORS TO TARGET DRUG-RESISTANT BACTERIA AND METHODS OF MAKING AND USING THE SAME, which claims the benefit of U.S. Provisional Patent Application No. 62/185,922, filed Jun. 29, 2015; Franz et al.; the disclosures of which are hereby incorporated by reference in their entireties.

STATEMENT REGARDING FEDERALLY SPONSORED RESEARCH OR DEVELOPMENT

This invention was made with government support under Grant No. GM084176 awarded by the National Institutes of Health and Grant No. CHE-1152054 awarded by the National Science Foundation. The United States Government has certain rights in the invention.

1. FIELD

The present disclosure provides antibacterial prodrugs and methods of making and using the same.

2. BACKGROUND 2.1. Introduction

While the widespread use of antibiotics since the 1940s has greatly reduced human morbidity and mortality, [1] bacterial resistance to these drugs has more than kept pace with antibacterial development. [2] From first-line treatments for routine infections to last resort antibiotics for life threatening infections, microbial resistance to antibacterial drugs is removing treatment options from doctors across the globe. Traditional antibiotics target a variety of processes that are essential for rapid bacterial growth, including inhibition of DNA/RNA synthesis (fluoroquinolones,) the depolarization of membrane potentials (daptomycin), inhibition of protein synthesis (aminoglycosides), [3] and inhibition of cell wall synthesis (β-lactams). Antibiotic resistance is achieved in a number of ways. With regard to the β-lactam class, some resistant bacteria produce enzymes called β-lactamases that selectively hydrolyze β-lactam antibiotics, rendering them ineffective at inhibiting cell wall biosynthesis. Thus, bacteria that produce β-lactamases can survive, or are resistant to, β-lactam antibiotics. [4] Alarmingly, bacterial resistance to β-lactam and other antibiotics continues to rise across the world. [5]

Antibiotic research has historically been directed at the discovery of new classes of broad-spectrum antibiotics. Recently, the search for new classes of antibiotics has been frustratingly slow. Indeed, since 1962 only two new classes of antibiotics have reached the market. [2] Conversely, the synthetic production of analogues to current antibiotics has been more fruitful. Indeed, the production of cephalosporin analogues has kept the cephalosporin class of antibiotics at the forefront of the fight against resistance. The downfall to this strategy is that there are a limited number of analogues for any particular class and that, given enough time, bacteria will develop resistance to each one.

The battle against antibacterial resistance is being waged on multiple fronts. By rotating through several rounds of different classes of antibiotics, alternating therapy has showed some promise. [6] Some scientists have begun searching for virulence targets rather than drugs that target viability. [3] Still, the world is in urgent need of new antibiotics and searching for new targets will take time. One potential solution is to develop an antibiotic that has multiple targets. Because it is harder for bacteria to develop resistance to multiple antibiotic mechanisms simultaneously, combination therapy or an antibiotic that has multiple targets should show increased activity and longevity.

Because metals play such important roles in cellular functions, their homeostasis presents a promising target for developing new antibiotics. [8, 9, 10] Numerous prescribed antibiotics have metal chelating properties and some metal chelators such as 2-mercaptopyridine N-oxide (pyrithione) and hydroxyquinolines are known to be bactericidal. [11, 12] However, metal ions are also necessary for normal mammalian cell function so systemic application of metal chelators can be problematic. In order to avoid undesired metal chelation, a number of prochelators have been developed that have little affinity for metals until they have been activated. [13, 14]

3. SUMMARY OF THE DISCLOSURE

Traditional antibiotics inhibit processes that are essential for rapid bacterial growth, including maintenance of membrane potentials and synthesis of DNA, RNA, proteins, and the bacterial cell wall. The β-lactam class of antibiotics, which inhibit cell wall biosynthesis, include some of the earliest antibacterial drugs introduced. While the widespread use of these antibiotics since the 1940s has greatly reduced human morbidity and mortality, unfortunately, bacterial adaptation to these drugs is outpacing antibacterial development. Alarmingly, bacterial resistance to β-lactams and other antibiotics continues to rise across the world. From first-line treatments for routine infections to last-resort antibiotics for life threatening infections, antibiotic resistance is removing treatment options from doctors across the globe.

Antibiotic resistance develops in a number of ways. With regard to the β-lactam class, resistant bacteria produce enzymes called β-lactamases that hydrolyze β-lactam antibiotics, rendering them ineffective at inhibiting cell wall synthesis. Thus, bacteria that produce β-lactamases can survive, or are resistant to, β-lactam antibiotics. Metal ions play important roles in processes that are essential for bacterial growth and virulence, but are also potentially toxic. This duality presents unmet opportunities to target bacterial processes associated with metal dependence and/or metal toxicity for developing new antibiotics. The basis of the current invention is the creation of prodrugs that conscript metal-dependent toxicity specifically against β-lactam-resistant bacteria by releasing metal chelators in response to β-lactamase activity.

The present disclosure provides, in part, an antibacterial prodrug that targets antibiotic resistant bacteria. The prodrug requires activation by an enzyme, such as bacterial β-lactamase enzymes, that selectively convert a non-toxic, non-metal binding prochelator into a toxic metal chelating agent that harnesses the metallobiology along the host-pathogen interface to exacerbate bacterial killing. See FIG. 13.

Disclosed herein is an antibacterial prochelator that targets antibiotic resistant bacteria comprising the following formula:

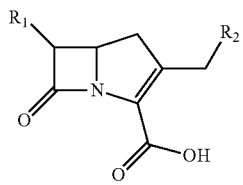

wherein $R_1$ is selected from the group consisting of:

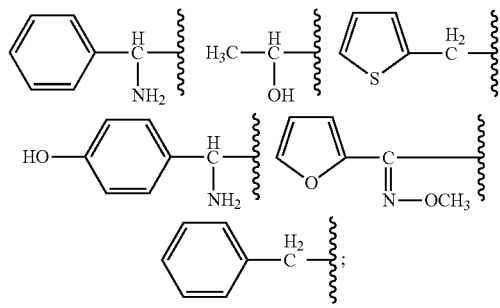

$R_2$ is

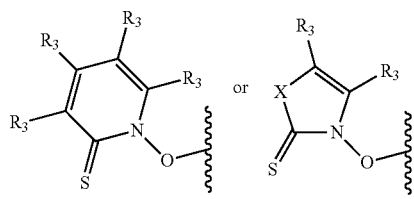

wherein each $R_3$ is alkyl, aryl, heteroaryl, H, OH, $NH_2$, SH or two adjacent $R_3$ may form a 5 or 6-member aromatic or heteroaromatic ring;
X is N-alkyl, NH, O or S; and any salts, or esters thereof.

Also disclosed is an antibacterial prochelator that targets antibiotic resistant bacteria comprising the following formula:

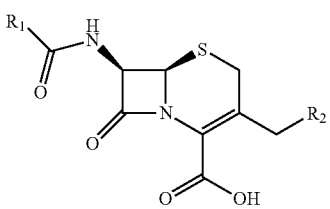

wherein $R_1$ is selected from the group consisting of:

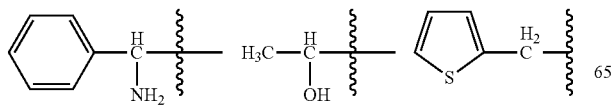

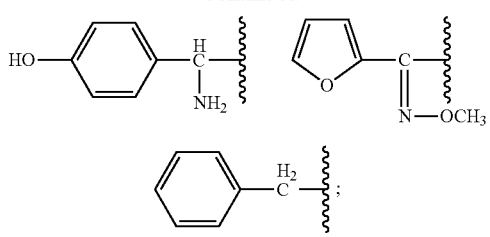

$R_2$ is

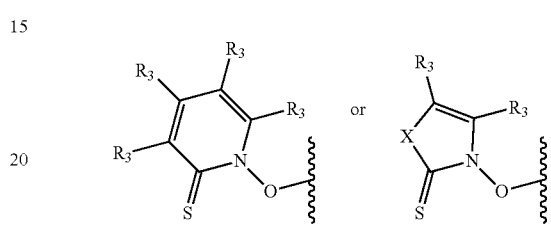

wherein each $R_3$ is alkyl, aryl, heteroaryl, H, OH, $NH_2$, SH or two adjacent $R_3$ may form a bicyclic moiety with a 5 or 6-member aromatic or heteroaromatic ring;
X is N-alkyl, NH, O or S; and any salts, or esters thereof.

The compound of the preceding paragraphs, wherein $R_1$ may be

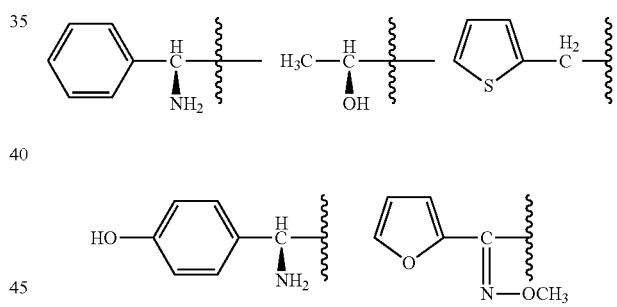

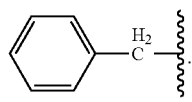

The compound of the preceding paragraphs, wherein $R_2$ may be

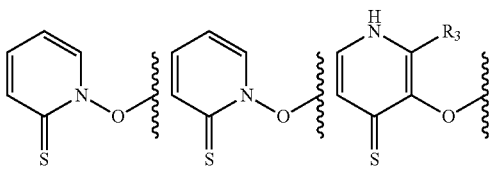

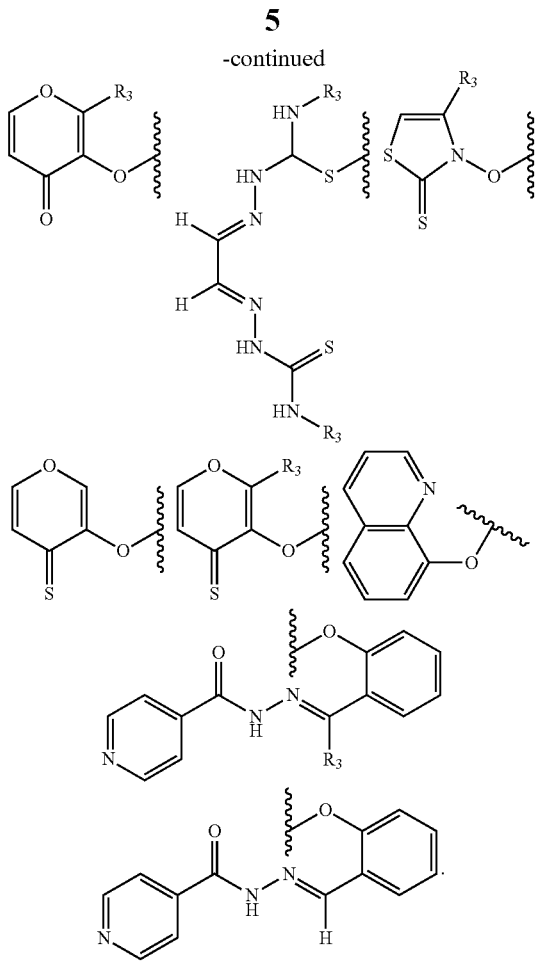

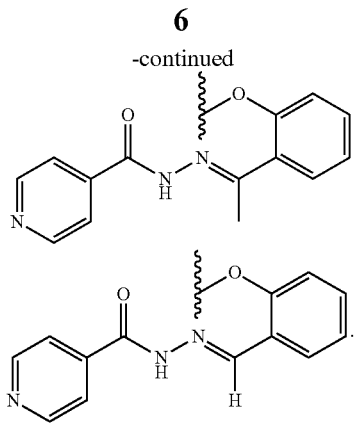

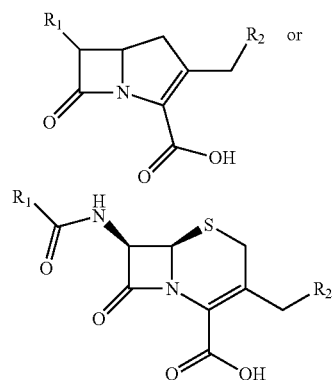

The compound of the preceding paragraph, wherein $R_2$ may be

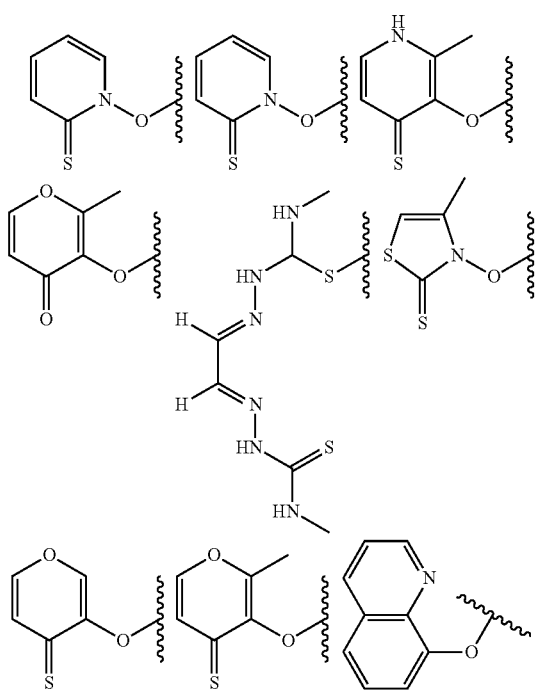

In an alternative embodiment, an antibacterial prochelator that targets antibiotic resistant bacteria comprising the following formula:

wherein $R_1$ is as defined above and $R_2$ may be

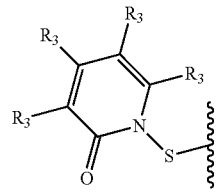

or more specifically

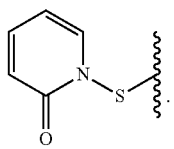 [SMILES: *Sn1ccccc1=O]

Also disclosed is an antibacterial prochelator comprising 2-((((6R,7R)-2-carboxy-8-oxo-7-(2-phenylacetamido)-5-thia-1-azabicyclo[4.2.0]oct-2-en-3-yl)methyl)thio)pyridine 1-oxide.

Also disclosed is an antibacterial prochelator comprising (6R,7R)-3-(((4-methyl-2-thioxothiazol-3(2H)-yl)oxy)methyl)-8-oxo-7-(2-phenylacetamido)-5-thia-1-azabicyclo[4.2.0]oct-2-ene-2-carboxylic acid.

A pharmaceutical composition comprising the compound of the preceding paragraphs and a pharmaceutically acceptable carrier.

A pharmaceutical composition comprising the prochelator of the preceding paragraphs and a metal salt.

The pharmaceutical composition of the preceding paragraph, wherein the metal salt is a copper, iron or zinc salt.

The pharmaceutical composition of the preceding paragraph, wherein the metal salt is a copper salt.

A method of treating a subject suffering from an infection from an antibiotic-resistant bacteria comprising the steps of administering to the subject a therapeutically effective amount of antibacterial prochelator of the preceding paragraphs such that the infection is treated.

The method of the preceding paragraph, further comprising administrating a metal salt.

A method of preventing or attenuating an antibiotic-resistant bacterial infection in a subject comprising administering to the subject a therapeutically effective amount of a antibacterial prochelator of any of the preceding paragraphs such that the infection is prevented or attenuated.

The method of the preceding paragraph, further comprising administrating a metal salt.

4. DETAILED DESCRIPTION OF THE DISCLOSURE

Figure 1:
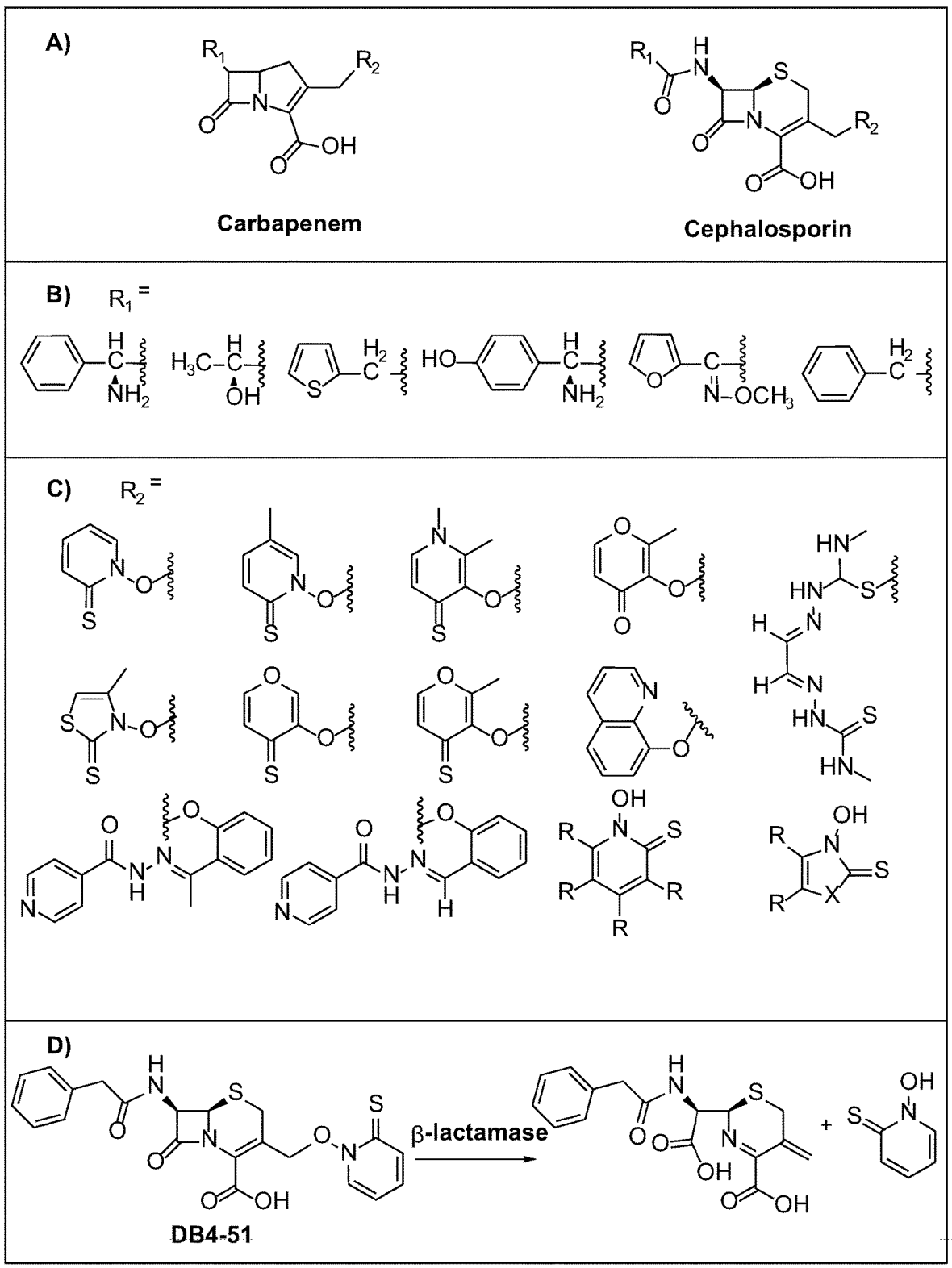
FIG. 1 is a schematic showing general structures of prochelators. Specifically, both carbapenam and cephalosporin β-lactam cores can be varied at the R1 and R2 positions in order to modify the selectivity to hydrolysis. Panel A) Both cores are reported to eliminate the R2 group upon β-lactam hydrolysis. Panel B) A sampling of R1 groups that have been used in commercial β-lactams to tune enzyme recognition and antibiotic activity. Panel C) The R2 groups illustrated are all metal chelating agents with various antimicrobial properties. Panel D) Activation of example prochelator DB4-51 by β-lactamase enzyme causes scission of the β-lactam and concomitant at the 3' position of pyrithione.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The present disclosure provides, in part, an antibacterial prodrug that targets antibiotic resistant bacteria. The prodrug requires activation by an enzyme, such as bacterial β-lactamase enzymes, that selectively convert a non-toxic, non-metal binding prochelator into a toxic metal chelating agent that harnesses the metallobiology along the host-pathogen interface to exacerbate bacterial killing.

Another aspect of the present disclosure provides a method of treating a subject suffering from an infection from an antibiotic-resistant bacteria comprising, consisting of, or consisting essentially of the steps of administering to the subject a therapeutically effective amount of antibacterial prodrug described herein such that the infection is treated.

4.1. Definitions

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with one or more halogens, e.g., trifluoromethyl. In certain embodiments, an alkyl group comprises from 1 to 20 carbon atoms. Alternatively, an alkyl group may comprise from 1 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen.

"Derivatives" refers to a precursor or modified form of a pharmaceutically active substance that is less bioactive compared to the parent drug and is capable of being enzymatically activated or converted into the more active parent. Derivative forms of the compounds described herein may designed to improve bioavailability or stability or reduce toxicity. For example, compounds of the invention having free amino, amido, carboxylic, hydroxyl, or thiol groups can be converted into derivatives. See Rautio et al., 2008 Nat Rev Drug Dis 7 255-270. For instance, free carboxyl groups can be derivatized as amides, carbamates, esters, or N-Mannich bases. Free hydroxy groups may be derivatized using groups including but not limited to carbonates, dimethylaminoacetates, ethers, hemisuccinates, phosphate esters, and phosphoryloxymethyloxycarbonyls, as outlined in Fleisher et al., 1996 Advanced Drug Delivery Reviews 19, 115-130. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Derivatives of this type are described in Robinson et al., 1996 J Med Chem 39 10-18. Free amines can also be derivatized as amides, carbamates, imines, N-Mannich bases, oximes, phosphonamides, or sulfonamides. Carbonyls may be derivatized to imine or oxime prodrugs. Thiols may be derivatized as esters or ethers. Derivatives may also include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes beta-alanine, citrulline, demosine, gamma-aminobutyric acid, homocysteine, homoserine, 4-hydroxyproline, hydroxylysine, isodemosine, 3-methylhistidine, norvalin, methionine sulfone, and ornithine.

"Electron donating group" (EDG) $CO_2H$, hydroxyl, $-NH_2$, $-NH_2$, $-SO_{(1-3)}H$, or $-SH$.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a saturated 5- to 7-membered heterocycle. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, benzodioxin, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

As used herein, the term "subject" and "patient" are used interchangeably and refer to any animal being examined, studied or treated. It is not intended that the present disclosure be limited to any particular type of subject. In some embodiments of the present invention, humans are the preferred subject, while in other embodiments nonhuman animals are the preferred subject, such as farm animals or pets, including but not limited to camels, cats, cattle, chickens, dogs, ferrets, goats, horses, mice, monkeys, pigs, rats, reptiles, sheep, or turkeys. In certain embodiments, the subject is suffering from an infection with an antibiotic-resistant bacteria.

"Substituted" refers to a group in which one or more hydrogen atoms are each independently replaced with the same or different substituent(s). Typical substituents include, but are not limited to, $CO_2H$, halogen (e.g., chloro, fluoro), hydroxyl, $-N_3$, $-NH_2$, $-SO_{(1-3)}H$, or $-SH$.

As used herein, the terms "treat", "treatment" and "treating" refer to the reduction or amelioration of the severity, duration and/or progression of a condition or one or more symptoms thereof resulting from the administration of one or more therapies. Such terms refer to a reduction of an antibiotic-resistant bacteria damage to a cell, tissue, organ, or whole organism, or a reduction and/or loss of function in the cell, tissue, organ or whole organism.

Yet another aspect of the present disclosure provides a method of preventing or attenuating an antibiotic-resistant bacterial infection in a subject comprising, consisting of, or consisting essentially of administering to the subject a therapeutically effective amount of a antibacterial prodrug described herein such that the infection is prevented or attenuated.

As used herein, the term "prevent" refers to the prevention of infection by an antibiotic-resistant bacteria. The term "attenuate" refers to the lessening or reduction of damage to a subject infected by an antibiotic-resistant bacteria.

4.2. Deuterated and Other Isotopic Variations

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Substitution with positron emitting isotopes, such as $^{11}C$, $^{18}F$, $^{15}O$ and $^{13}N$, can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. Alternatively, deuterium may be also incorporated into a compound using methods such as through reduction such as using $LiAlD_4$ or $NaBD_3$, catalytic hydrogenation or acidic or basic isotopic exchange using appropriate deuterated reagents such as deuterides, $D_2$ and $D_2O$. In addition to the above, PCT publications, WO2014/169280; WO2015/058067; U.S. Pat. Nos. 8,354,557; 8,704,001 and US Patent Application Publication Nos.; 20100331540; 20140081019; 20140341994; 20150299166, the methods are hereby incorporated by reference.

4.3. Pharmaceutically Acceptable Compositions

The disclosure also provides pharmaceutical compositions comprising an effective amount of the prodrugs described herein (e.g., any of the formulae and/or structures disclosed herein), or a pharmaceutically acceptable salt of said compound; and a pharmaceutically acceptable carrier.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866 (Infeld et al.); and US Pat. Pubs. 20060094744 (Maryanoff et al.) and 20060079502 (Lang).

The pharmaceutical compositions of the disclosure include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product. In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031 (Rabinowitz & Zaffaroni).

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene or polyoxypropylene compounds, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the therapeutics may be local, so as to be administered at the site of interest. Various techniques can be used for providing the compositions at the site of interest, such as injection, use of catheters, trocars, projectiles, pluronic gels, stents, sustained drug release polymers or other devices which provide for internal access. Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat.

No. 6,099,562 (Ding & Helmus); U.S. Pat. No. 5,886,026 (Hunter et al.); and U.S. Pat. No. 5,304,121 (Sahatjian). The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active. Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

It is to be understood that the invention is not limited in its application to the details of construction and the arrangement of components set forth in the following description or illustrated in the following drawings. The invention is capable of other embodiments and of being practiced or of being carried out in various ways.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The following examples are illustrative only and are not intended to be limiting in scope.

5. EXAMPLES

The approach disclosed here is innovative because it exploits the unique chemical milieu created by the enzymatic reactivity of antibiotic-resistant bacteria to conditionally release toxic metal-binding agents. These metal-binding agents exacerbate microbial killing by exploiting the metallobiology at the site of infection. The premise for the current invention is a prodrug approach in which a prochelator antibiotic is activated by β-lactamase enzymes to release a toxic metal chelator at the site of the resistant bacteria (FIG. 1 panel D). This approach allows for conditional release of a metal chelator at the site of bacterial infection, thereby sparing uninfected tissues from exposure to the toxic metal-chelator combination.

The design of these prochelators incorporates two activities into one antibiotic. The cephalosporin backbone acts as the masking group as well as a broad-spectrum antibiotic. The cephalosporin may be cleaved in the presence of gram-negative bacteria, which would likely kill the bacteria through the normal inhibition of cell wall biosynthesis. The real advantage to this approach is apparent in the presence of β-lactam-resistant bacteria. Instead of being inactivated by the hydrolysis of β-lactamases, this prochelator would be triggered to release a chelator with its own antibiotic activity. [9, 15, 16] The cephalosporin core has been well-studied for its propensity to eliminate at the 3' position upon scission of the β-lactam. [17]

Variations of β-lactam prodrug strategy have been reported in the literature. The conjugation of the cephalosporin core with 5-fluorouracil was reported to selectively release this colorectal drug in the presence of β-lactamase. [18] Efforts to visualize β-lactamases have produced molecules that release fluorophores upon hydrolysis of the β-lactam and subsequent elimination at the cephalosporin 3' position. [19, 20] Notably, a cephalosporin analogue similar to DB4-51 was reported in the patent and research literature in 1975 to release pyrithione in response to a commercial β-lactamase. [21, 22] These studies did not design prochelators utilizing the properties of resistant-bacteria to specifically release high concentrations of targeted metal chelator. The compounds described herein overcome the metal-dependent toxicity of the released pyrithione. Previous work did not disclose other chelating moieties. Any analogs they disclose were focused on variations of conventional mechanism of inhibiting cell wall biosynthesis. In contrast, our molecules are rationally designed pro-chelators, designed to be recognized by multiple forms of resistant bacteria. They are pro-drugs activated by β-lactamase resistant bacteria to releasing an agent like pyrithione, 8-hydroxyquinoline, thiomaltol or other chelators, see FIG. 1. The compounds described herein alter metal distribution in cells or potentially inhibit bacterial metallo enzymes including beta-lactamases. In addition, some of the compounds described herein have been adapted to modulate the levels of copper within the bacteria. Lastly, the compounds herein may be used in combination with metal salts, such as copper.

Using this approach, numerous analogs can be produced in which different chelating units are placed at the 3' position. Some examples are shown in FIG. 1. Analogs containing different chelators could have distinct affects against microbes on the basis of their unique metallobiology. The chelators 8-quinolinol 98-hydroxyquinoline, 8HQ) and pyrithione have been shown to have antimicrobial activity that is enhanced in the presence of copper. [23, 24] Interestingly, the chelator 3-hydroxy-2-methyl-4H-pyran-4-thione (thiomaltol) has been reported to inhibit the activity of metallo-β-lactamases, likely via coordination to the active site zinc ions. [25] Inclusion of thiomaltol or similar units at the cephalosporin 3' position promises to be a unique delivery system of thiomaltol to the enzyme active site to facilitate its binding to the zinc active-site. Iron chelators can also demonstrate antibacterial activity by sequestering required iron from the pathogen. Several of the example derivatives shown in FIG. 1 Panel C are potent iron chelators.

5.1. Design of DB4-162

The prochelator DB4-162 was designed using the same prochelator strategy upon which DB4-51 was based. A cephalosporin core was elaborated at the 3' position with 3-hydroxy-4-methyl-2(3H)-thiazolethione (TAT) which, like other cyclic thiohydroxamic acids, has been investigated for its metal-binding and antimicrobial properties.[30, 31] DB4-162 was designed to be unmasked in the presence of the β-lactamase enzyme in order to deliver its chelator payload at the site of bacterial infection. There is no known account of using a cephalosporin as the protecting group for TAT in a prochelator approach to selectively manipulate metals at the site of bacterial infection.

Although the antimicrobial activity of TAT is not well-studied, it was incorporated into the prochelator design based on the results of our antimicrobial screening assay. TAT is able to inhibit the growth of a number of pathogenic bacteria. The observed antimicrobial activity of TAT may be related to its metal affinity. TAT possesses the same thiohydroxamic acid O, S bidentate binding site as pyrithione and, as such, it is not surprising that TAT has the ability to form complexes with various metal ions such as Cu2+, Zn2+, Co2+, and Ni2+.[32, 33, 34] However, an in-depth study on the metal-affinity of TAT has not been reported. [35]

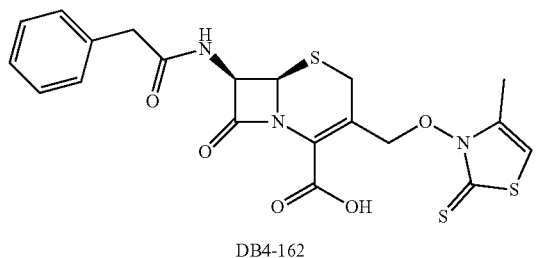 [SMILES: Cc1csc(=S)n1OCC1=C(C(=O)O)N2C(=O)[C@@H](NC(=O)Cc3ccccc3)[C@H]2SC1]

DB4-162

In addition to what is known about TAT, similar thiol-containing triazoles such as 4-methyl-5-(tri-fluoromethyl)-4H-1,2,4-triazole-3-thiol (1) and 5-methyl-4H-1,2,4-triazole-3-thiol (2) have been reported to behave as both competitive and uncompetitive inhibitors of the metallo-β-lactamase (MBL) IMP-1 by binding in the zinc-containing active site of the enzyme as well as forming a tertiary complex with the enzyme. [36] This binding inhibits the zinc-containing metallo-enzyme from hydrolyzing β-lactam substrates. [37] Structure-activity relationship studies have shown that the thiol group in these triazole compounds is required for activity.

4-methyl-5-(tri-fluoromethyl)-4H-1,2,4-triazole-3-thiol, 5-methyl-4H-1,2,4-triazole-3-thiol, 5-methyl-1,3,4-thiadiazole-2(3H)-thione and 3-hydroxy-4-methyl-2(3H)-thiazolethione (TAT) are 4 compounds that have demonstrated metal affinity and are being investigated as inhibitors of MBL-activity. [38]

Of particular relevance is the recent work in which cephalosporin conjugates containing heterocyclic thiones such as 5-methyl-1,3,4-thiadiazole-2(3H)-thione were studied for their ability to inhibit the activity of the MBL-catalyzed hydrolysis of cephalosporins. These studies determined that thione-containing compounds are able to chelate Zn2+ ions and form relatively stable complexes with a Zn2+ metal center. Thus, cephalosporin-thione conjugates like cephazolin were able to slow the hydrolytic activity of MBL. This result suggests that compound like cephazolin that release thiones in proximity to MBL may play a significant role in designing new antibiotics that target MBL-producing bacteria.

While high-throughput screening has identified a number of potential MBL-inhibitors that have affinity for zinc, not all zinc-binding groups are successful inhibitors. However, the demonstrated antibacterial activity of TAT combined with its structural similarity to known inhibitors of the resistance-causing MBL enzymes made the compound worth exploring. TAT was therefore incorporated into a second prochelator, DB4-162.

5.2. Materials and Methods

The starting material 7-amino-3-chloromethyl-3-cephem-4-carboxylic acid p-methoxybenzyl ester was purchased from Ark Pharm Inc. (Libertyville, Ill.) in reagent grade and was used without further purification. Type III β-lactamase from *Enterobacter cloacae* was purchased from Sigma Aldrich Corp. (St. Louis, Mich.). All other reagents were purchased from Sigma Aldrich unless otherwise stated. All solvents were reagent grade and all aqueous solutions were prepared from nanopure water. Compound stock solutions were prepared in DMSO and stored at −20° C. $^1$H NMR and $^{13}$C NMR spectroscopy were performed on a Varian 400 or 500 MHz spectrometer. ESI/LC-MS spectra were collected on an Agilent 1100 Series spectrometer utilizing an electrospray ionization source, an LC/MSD trap, and a Daly conversion dynode detector. ICP-MS data were acquired using a Perkin Elmer Elan DRCII spectrometer. UV-Vis spectra were recorded on a Cary 50 UV-Vis spectrophotometer. $OD_{600}$ readings were measured using clear, flat-bottom 96-well plates and a Perkin Elmer Victor 3V multi-label counter maintained at 25° C. HPLC purification was performed on a Waters 600 system with a Waters X-Bridge 4.6×250 mm, C18 column using a water/acetonitrile mobile phase.

5.3. Synthesis

5.3.1. Synthesis of DB4-51

4-methoxybenzyl (6R,7R)-3-(chloromethyl)-8-oxo-7-(2-phenylacetamido)-5-thia-1-azabicyclo[4.2.0]oct-2-ene-2-carboxylate (2)

To a portion of 1 (1.2 g, 2.96 mmol) was added dichloromethane (50 mL) under a dry $N_2$ atmosphere to form a tan slurry. The reaction mixture was cooled to 0° C. in an ice bath and potassium trimethylsilanolate (760 mg, 5.92 mmol, 2 equiv) was added slowly and stirred for 5 min. To the reaction mixture was added phenylacetyl chloride (431 µL, 3.26 mmol, 1.1 equiv) while stirring. After 1 h the reaction mixture was removed from the ice bath and stirred at room temperature for 4 h. The reaction mixture was concentrated in vacuo before the addition of dichloromethane (20 mL). The organic phase was washed with water (2×10 mL) rejecting any precipitate in the aqueous layer. The organic layer was washed with brine (10 mL) and dried over $MgSO_4$. The volatile components were removed via rotary evaporation to yield a tan solid (1.2 g, 2.51 mmol, 85%) which was used without further purification. $^1H$ NMR (DMSO-$d_6$, 400 MHz) δ (ppm): 7.37 (d, J=8.4 Hz, 2H), 7.29-7.27 (m, 5H), 6.94 (d, J=8.8 Hz, 2H), 5.75-5.71 (q, J=4 Hz, 1H), 5.24-5.14 (m, 4H), 4.55-4.43 (q, J=12 Hz, 2H), 3.75 (s, 3H), 3.69 (s, 1H), 3.58-3.50 (m, 3H). $^{13}C$ NMR (DMSO-$d_6$, 500 MHz) δ (ppm): 173.14, 171.37, 165.56, 161.57, 159.82, 136.22, 135.47, 130.81, 129.82, 129.64, 129.46, 128.80, 128.69, 127.03, 126.97, 125.75, 114.27, 114.10, 67.81, 59.65, 58.35, 44.28, 42.06, 41.15. HR-MS (ESI) (m/z): $[M+Na]^+$ calcd for $([C_{24}H_{23}ClN_2O_5S]+Na)^+$, 509.0908, found 509.0909.

2-((((6R,7R)-2-(((4-methoxybenzyl)oxy)carbonyl)-8-oxo-7-(2-phenylacetamido)-5-thia-1-azabicyclo[4.2.0]oct-2-en-3-yl)methyl)thio)pyridine 1-oxide (3)

A mixture of 2-mercaptopyridine N-oxide (21 mg, 0.17 mmol) and triethylamine (17 mg, 0.17 mmol, 1 equiv) was dissolved in THF (4 mL) and stirred at 25° C. for 15 min. To the reaction mixture was added 2 (75 mg, 0.15 mmol, 0.9 equivs) and the reaction was allowed to stir for 1 h yielding a dark orange solution. The reaction mixture was diluted with ethyl acetate and washed with saturated $NaHCO_3$ before drying over $MgSO_4$. The volatile components were removed via rotary evaporation to yield a yellow glassy solid (45 mg, 0.08 mmol, 50%) which was purified on a C18 column via HPLC in $H_2O$/ACN. $^1H$ NMR (DMSO-$d_6$, 400 MHz) δ (ppm): 8.29 (s, 1H), 7.18-7.30 (m, 11H), 6.76-6.87 (m, 2H), 5.06-5.17 (m, 3H), 3.97-3.98 (d, J=0.4 Hz, 2H), 3.68-3.70 (d, J=8.4 Hz, 4H), 3.47-3.57 (m, 3H), 2.04 (s, 3H). $^{13}C$ NMR (DMSO-$d_6$, 500 MHz) δ (ppm): 171.39, 165.35, 161.89, 159.75, 150.24, 138.74, 136.22, 130.79, 130.71, 129.53, 129.45, 128.69, 127.35, 126.96, 126.20, 125.91, 125.50, 122.82, 122.06, 114.33, 114.19, 67.69, 59.58, 58.39, 55.55, 42.06, 42.00, 32.81, 27.89. HR-MS (ESI) (m/z): $[M+Na]^+$ calcd for $([C_{29}H_{27}N_3O_8S_2]+Na)^+$, 600.1233, found 600.1233.

2-((((6R,7R)-2-carboxy-8-oxo-7-(2-phenylacetamido)-5-thia-1-azabicyclo[4.2.0]oct-2-en-3-yl)methyl)thio)pyridine 1-oxide (DB4-51)

Portions of 3 (71 mg, 0.12 mmol) and phenol (232 mg, 2.46 mmol, 20 equivs) were stirred at 45° C. over an oil bath for 15 min. Trifluoroacetic acid (14 µL, 0.19 mmol, 1.5 equivs) and continued stirring for 1.5 h before the volatile components were removed via rotary evaporation. The resulting yellow oil was mixed with ethyl acetate (10 mL) and extracted with saturated $NaHCO_3$ (2×10 mL). The aqueous phase was cooled in an ice bath and titrated with 10% HCl to pH=1. The aqueous layer was then extracted with ethyl acetate which was dried over $MgSO_4$. The volatile components were removed via rotary evaporation to yield a yellow powder. The solid was washed with ether and dried under vacuum to yield a white powder (30 mg, 0.07 mmol, 53%) which was used without further purification. $^1H$ NMR (DMSO-$d_6$, 400 MHz) δ (ppm): 8.26 (t, J=5.2 Hz, 1H), 7.18-7.40 (m, 9H), 6.70 (s, 1H), 5.11 (m, 1H), 3.67-4.04 (m, 2H), 3.43-3.51 (t, J=15.6 Hz, 3H). $^{13}C$ NMR (DMSO-$d_6$, 500 MHz) δ (ppm): 171.41, 165.15, 163.46, 150.59, 138.74, 136.27, 129.48, 128.69, 126.96, 126.65, 125.97, 125.45, 122.67, 121.98, 59.51, 58.23, 42.06, 32.76, 27.78. HR-MS (ESI) (m/z): $[M+H]^+$ calcd for $C_{21}H_{19}N_3O_5S_2$, 458.0839, found 458.0835.

5.3.2. Synthesis of DB4-162

Preparation of 4-methoxybenzyl (6R,7R)-3-(chloromethyl)-8-oxo-7-(2-phenylacetamido)-5-thia-1-azabicyclo[4.2.0]oct-2-ene-2-carboxylate (2)

Intermediate 2 was prepared from the commercial starting material 1 as described above.

Preparation of 4-methoxybenzyl (6R,7R)-3-(((4-methyl-2-thioxothiazol-3(2H)-yl)oxy)methyl)-8-oxo-7-(2-phenylacetamido)-5-thia-1-azabicyclo[4.2.0]oct-2-ene-2-carboxylate (4)

A portion of 3-hydroxy-4-methyl-2(3H)-thiazolethione (100 mg, 0.68 mmol) was dissolved in THF (9 mL) with triethylamine (69 mg, 0.68 mmol, 1.1 equivs) and the solution was stirred under dry N2 for 15 min. To the reaction mixture was added 2 (0.29 g, 0.61 mmol, 0.9 equivs) and stirred under dry $N_2$ for 4 h when a precipitate had formed. The mixture was vacuum filtered and the precipitate was washed with THF and acetone. The filtrate was reduced under vacuum to leave a brown residue. The resulting solid was dissolved in ethyl acetate and washed with NaHCO3 and brine before drying over MgSO4. The volatile components were removed via rotary evaporation to yield a glassy solid. The solid was purified via column chromatography on silica gel solid phase with 2-4% methanol in dichloromethane. Volatile components were removed via rotary evaporation to yield the isolated intermediate in good yield (0.28 g, 0.47 mmol, 77%). 1H NMR (CDCl3, 400 MHz) δ (ppm): 7.30-7.35 (m, 5H), 6.97 (s, 1H), 6.86-6.88 (m, 4H), 5.99-6.09 (dd, J=31.2, 9.2 Hz, 2H), 5.76-5.79 (q, J=4.8 Hz, 1H), 5.11-5.13 (d, J=9.2 Hz, 5H), 4.90-4.91 (d, J=4.8 Hz, 1H), 4.11-4.28 (dd, J=13.2, 54.8 Hz, 2H) 3.61 (m, 4H), 2.31-2.32 (d, J=4.8 Hz, 5H). 13C NMR (DMSO-$d_6$, 500 MHz) δ (ppm): 171.37, 161.47, 159.79, 145.62, 136.22, 130.79, 130.62, 129.53, 129.45, 128.68, 126.96, 126.70, 125.08, 114.33, 114.24, 67.69, 59.53, 58.39, 55.60, 50.24, 35.13, 27.78, 13.55. HR-MS (m/z): [M+Na]+ calcd for $C_{28}H_{27}N_3O_6S_3$, 620.0954, found 620.0957.

Preparation of (6R,7R)-3-(((4-methyl-2-thioxothiazol-3(2H)-yl)oxy)methyl)-8-oxo-7-(2-phenylacetamido)-5-thia-1-azabicyclo[4.2.0]oct-2-ene-2-carboxylic acid (DB4-162)

A portion of 4 (84 mg, 0.14 mmol) and phenol (264 mg, 2.81 mmol, 20 equivs) stirred at 45° C. over an oil bath for 15 min. Added trifluoroacetic acid (16 μL, 0.21 mmol, 1.5 equivs) and continued stirring for 2 h before the volatile components were removed via rotary evaporation. The resulting yellow oil was mixed with ethyl acetate (10 mL) and extracted with saturated NaHCO3 (2×10 mL). The aqueous phase was cooled in an ice bath and titrated with 10% HCl to pH=1. A white precipitate formed that was collected via vacuum filtration and washed with acidified H2O and acetone. The precipitate was dried under vacuum to yield a white powder (20 mg, 0.04 mmol, 29%) which was used without further purification. 1H NMR (DMSO-d6, 400 MHz) δ (ppm): 9.12 (d, J=8.2 Hz, 1H), 7.68 (s, 1H), 7.31-7.19 (m, 5H), 5.61 (dd, J=8.1, 4.7 Hz, 1H), 4.99 (d, J=4.7 Hz, 1H), 4.25 (d, J=12.9 Hz, 2H), 3.94 (d, J=12.9 Hz, 1H), 3.77-3.58 (m, 3H), 3.58-3.44 (m, 3H), 2.20 (s, 3H), 2.06 (s, 1H), 1.23-1.09 (m, 2H). 13C NMR (DMSO-d6, 500 MHz) δ (ppm): 171.44, 164.99, 162.98, 145.42, 136.29, 129.50, 128.70, 126.97, 126.58, 125.42, 116.30, 59.51, 58.19, 42.04, 35.66, 27.58, 13.57. HR-MS (ESI) (m/z): [M+H]+ calcd for $C_{20}H_{19}N_3O_5S_3$, 478.0560, found 478.0556.

5.3.3. Bacterial Cultures

Bacterial culture reagents including LB broth (Lennox), agar-agar, ampicillin, and ceftriaxone were purchased from Sigma Aldrich Corp. The *Escherichia coli* (*E. coli*) K12 strain HB101 and pGLO *E. coli* transformation kit purchased from Bio-Rad Laboratories Inc. [26] HB101 was transformed with the bla gene via the pGLO plasmid. The bla gene encodes for a TEM-1 β-lactamase that imparts penicillin resistance to the mutant *E. coli* K-12 strain (+Bla). Strains *E. coli* UTI89, [27] pCOM-GFP-transformed *E. coli* UTI89 (pCOM-GFP), [28] and Methicillin-Resistant *Staphylococcus aureus* (MRSA) clone USA300 [29] have been previously described. The Extended-Spectrum β-Lactamase (ESBL) *E. coli, Klebsiella pneumonia* (Klebs), and *Pseudomonas aeruginosa* (Pseudo) strains were clinical isolates acquired deidentified from Duke Hospital and tested for antibiotic susceptibility in the Clinical Microbiology Laboratory using standard clinical susceptibility methods.

5.3.4. Microdilution Screening of Compounds in Bacteria

Cultures were incubated on LB (Lennox, Sigma) agar at 37° C. in ambient atmospheric composition. Before beginning an experiment, a single bacterial colony grown on LB agar was resuspended in 2 mL LB broth and incubated overnight to form a turbid cell suspension. The overnight culture was diluted 1:100 in LB and used immediately as the working culture. To assess the antibacterial activity of compounds, the working bacterial culture was aliquoted in a clear, flat-bottomed, 96-well polystyrene plate (Costar) and the compound of interest was added in 2-fold serial dilution from 500 to 1 μM. Plates were covered with a breathable sealing film (Aeroseal, Genesee Scientific) and incubated at 37° C. in ambient atmospheric composition with shaking at 200 rpm. Optical density at 600 nm was recorded after 4 h and 20 h for each well using a standard $OD_{600}$ protocol with LB serving as the blank. The resulting dose-response curves were fit to a nonlinear regression in GraphPad Prism Version 6 to calculate the $IC_{50}$ of DB4-51 in each strain.

5.3.5. LC-MS Detection of DB4-51 in Bacterial Media

Cultures of UTI89 and ESBL *E. coli* as well as *K. pneumoniae* clinical isolates 4 and 9 were grown in LB overnight at 37° C. and then diluted 1:100 in LB containing 100 μM DB4-51. These cultures were incubated for 1-4 hours at 37° C. while shaking at 200 rpm. After incubating, aliquots were removed from each culture and centrifuged at 15,000 rpm for 5 min to pellet the bacteria. The pellets were resuspended in sterile water and centrifuged again after which the supernatant was decanted and collected. A 5-fold excess (v/v) of cold acetone was added and the samples were cooled to −20° C. for 1 h before centrifuging at 8,500 rpm for 10 mins to remove proteins. The supernatant was decanted and the pellet was washed with cold acetone and centrifuged again. The combined supernatants were reduced to dryness via rotary evaporation. Each LC-MS sample was prepared by dissolving the dry samples above in 85/15 water/ACN. LC-MS was performed on the samples using a 2-60% ACN gradient in $H_2O$ over 18 min. Rofecoxib (10 μM, Sigma) was included as an internal standard. The integrated area under the absorbance peak that corresponds with the mass of the prochelator was compared to a calibration curve to calculate the concentration of prochelator present after incubation.

5.3.6. Mammalian Culture

Cell culture reagents including minimal essential medium (MEM), fetal bovine serum (FBS), penicillin streptomycin (pen-strep), Triton X-100, and 0.25% trypsin-Ethylenediaminetetraacetic acid (EDTA) were purchased from Gibco. CellTox Green LDH Cytotoxicity Detection Kit was purchased from Promega. Cell lines were purchased from the ATCC. All work was performed in a laminar-flow hood using sterile techniques. Human lung fibroblast cells (CCD-19Lu, ATCC CCL-210) and human liver epithelial cells (HepG2, ATCC HB-8065) were allowed to adhere overnight to a clear, tissue-culture treated, flat-bottom, 96-well plate in MEM with glutamine and pyruvate supplemented with 10% (v/v) FBS and 1% non-essential amino acids. After splitting and counting, black, clear bottom 96-well plates were seeded at a density of 15,000 cells/well and incubated overnight at 37° C. in a fully humidified atmosphere containing 5% $CO_2$. The growth medium was replaced with serum-free medium containing CellTox Green dye and serial dilutions of the active compounds in the presence and absence of 10 μM $CuCl_2$ (Sigma). After 24 h incubation, the fluorescence emission at 520 nm was recorded (excitation at 485 nm). Untreated cells served as the negative control while wells containing untreated cells incubated with 1% Triton X-100 served as the positive control.

5.4. Results

Prochelator DB4-51 was synthesized by following the procedure shown in Scheme 1, using 7-amino-3-chloromethyl-3-cephem-4-carboxylic acid p-methoxybenzyl ester as the starting material. This cephalosporin core is easily varied at the C-7 and C-3 positions. Amidation of the C-7 amine was achieved with phenylacetyl chloride. As previously reported, potassium trimethyl silanolate was used to avoid the formation of Δ2 isomer. [18] The 3' chloride was then displaced using the thiolate of pyrithione to yield compound 3 that was purified vla HPLC. Acidic deprotection to remove the p-methoxybenzyl group afforded the title compound. LC-MS and 1H NMR spectroscopy were used to confirm the identity of compound DB4-51.

Scheme 1:

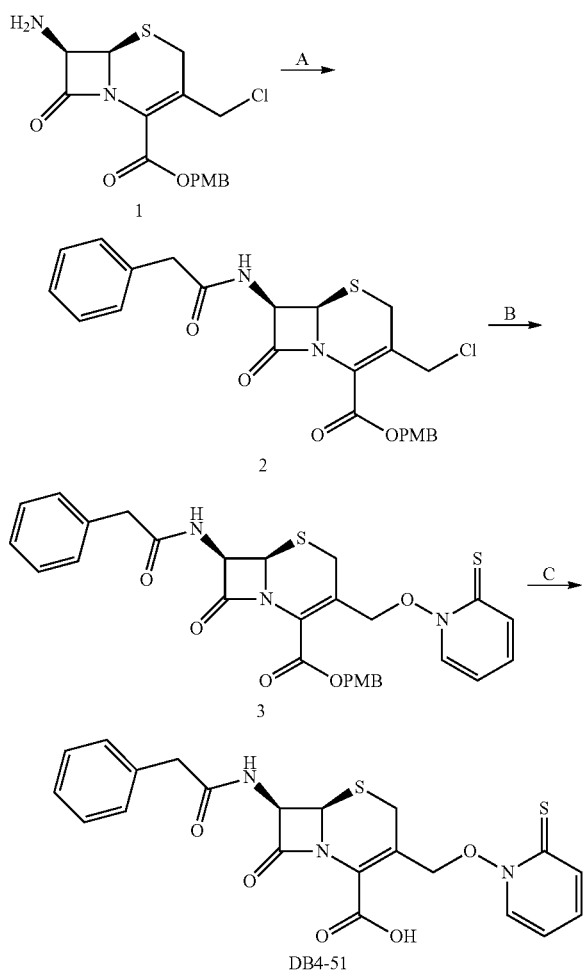

Scheme 1: Synthesis of DB4-51.

A) Phenylacetyl chloride, KOSiMe₃, DCM, rt, 75%;
B) pyrithione, TEA, THF, rt, 75%; C) TFA, phenol. 53%.

Scheme 2:
Scheme 2: Synthesis of DB4-162

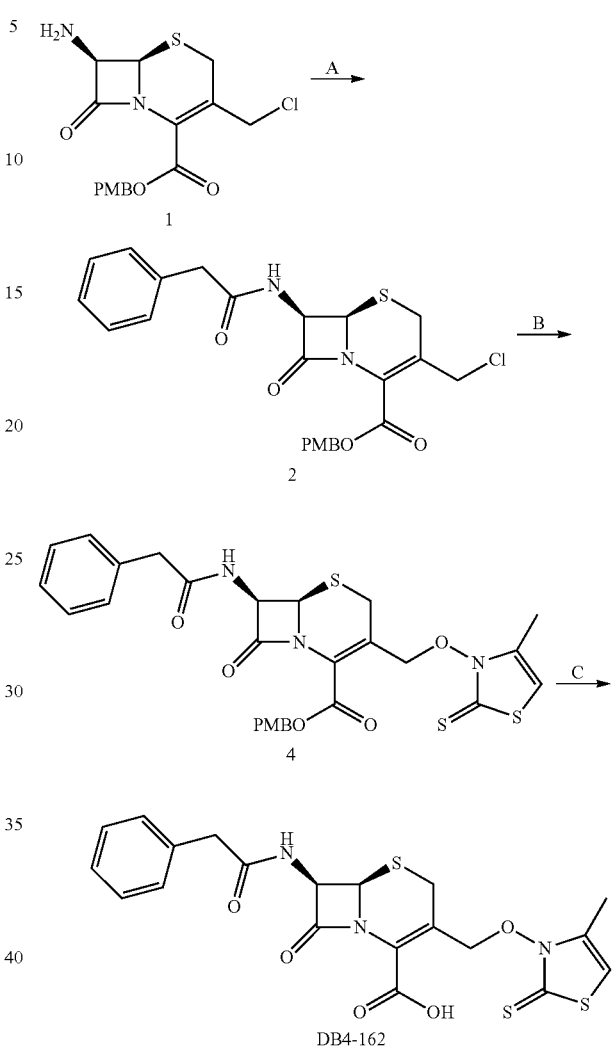

A) Phenylacetyl chloride, KOSiMe₃, DCM, rt, 75%;
B) thiazolethione, Et3N, THF, rt, 77%; C) TFA, phenol, 29%.

Scheme 3 shows a synthesis of prochelator DB4-41 which contains 8-hydroxyquinoline (8HQ) at the cephalosporin 3' position. BHQ is a known copper chelator with antibacterial properties. The synthesis of DB4-41 proceeds via a 3' iodide intermediate.

Scheme 3

Scheme 3: Proposed synthesis of DB4-41.

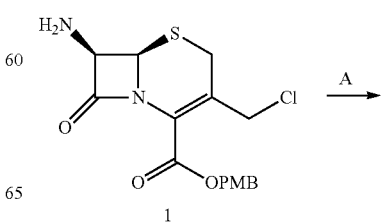

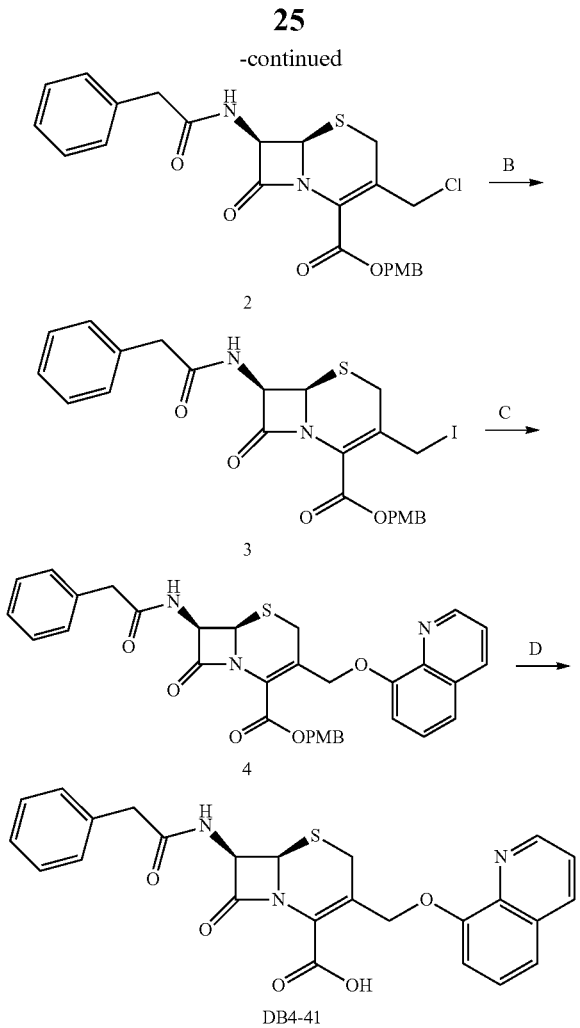

DB4-41

A) Phenylacetyl chloride, KOSiMe$_3$, DCM, rt, 75%; B) NaI, dry acetone, rt, 94%: C) K$_2$CO$_3$, 8-hydroxyquinoline. ACN, rt, 14%; D) TFA, phenol, 14%.

5.4.1. β-Lactamase Selectively Converts Prochelator

Figure 2:
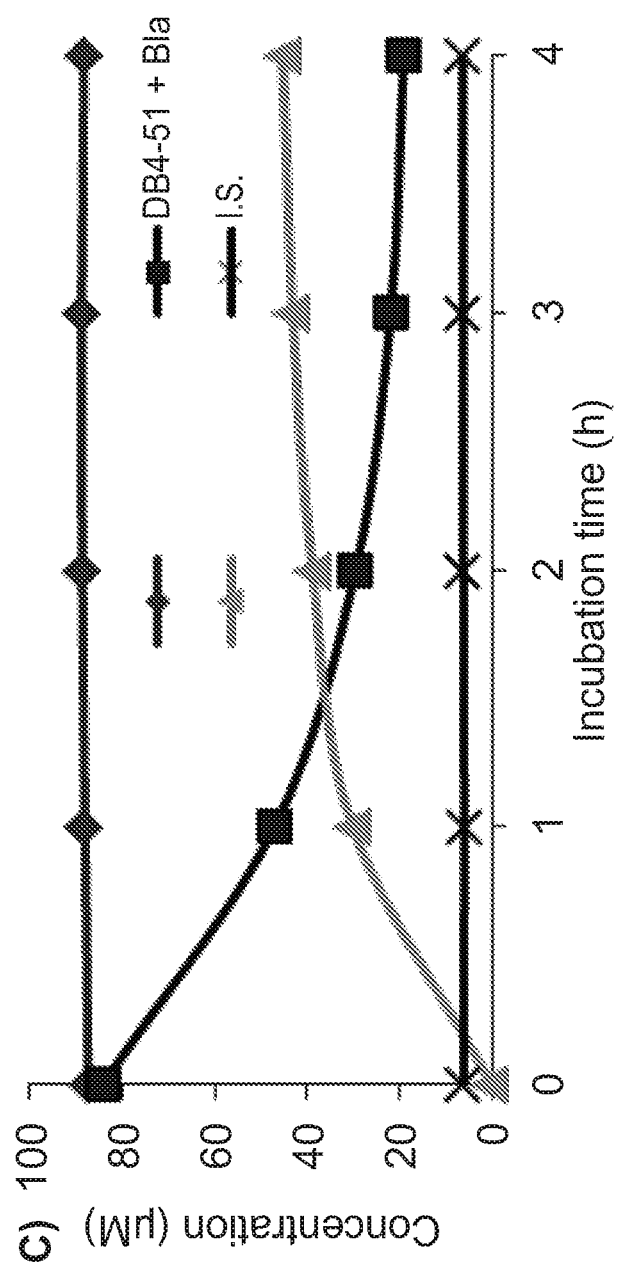
FIG. 2 is a graph showing the stability of 100 μM DB4-51 with and without β-lactamase.

A commercially available β-lactamase (type III from *Enterobacter cloacae*, Sigma Aldrich) was used to verify the specificity of compound DB4-51 activation. Aqueous samples of the prochelator with and without β-lactamase were incubated at 25° C. and LC-MS was performed periodically to monitor the conversion. The results are shown in FIG. 2. Percent conversion was calculated based upon the area under the LC-MS peak that corresponds to the mass of DB4-51. The results show ~80% conversion after 4 hours in the presence of a β-lactamase and ≤5% conversion after 48 hours in the absence of the enzyme. These results suggest that in aqueous environments the prochelator will persist until hydrolyzed by a β-lactamase.

FIG. 2 shows the stability of 100 μM DB4-51 with and without 0.5 units/ml β-lactamase in pH 7.4 PBS as monitored by LC-MS using a 2-30% ACN gradient over 17 minutes.

5.4.2. β-Lactamase Activity is Required to Activate the Prochelator

The results from the growth inhibition assays support our hypothesis that β-lactamase-producing bacteria activate DB4-51 to release PT as the active agent. To confirm this chemical reactivity, we performed in vitro spectroscopic and chromatographic assays to demonstrate that DB4-51 is stable in aqueous media but releases PT in the presence of β-lactamase. The UV-Vis absorbance spectra of DB4-51 and PT in PBS buffer are clearly distinct, with DB4-51 showing a shoulder at 264 nm and a broad absorption peak centered at 315 nm. The absorbance spectrum of DB4-51 in PBS remains unchanged after 19 hours, and the prochelator remains intact with no signs of degradation observed by LC-MS, even after incubating for 72 hours at 37° C. In contrast, incubation of DB4-51 with a type III TEM β-lactamase in vitro produces an absorbance spectrum matching that of PT, suggesting a clean release of PT from DB4-51 upon reaction with the enzyme.

LC-MS analysis of the reaction mixture of DB4-51 and β-lactamase confirms the result observed by spectrophotometry. The chromatographic peak area corresponding to DB4-51 decreases by more than 80% after 4 hours in the presence of β-lactamase. At the same time, a new peak appears earlier in the chromatogram with a mass spectral signal consistent with PT. Although the area under the PT peak suggests that only 50% of PT is released from the prochelator, it should be noted that standard PT samples themselves appear as a single chromatographic peak with corresponding m/z values that indicate a mixture of the monomeric thione form, disulfide form, and the 2:1 complex with Fe(III). Because its extinction coefficient varies depending on its state, PT is difficult to quantify chromatographically.[61] This observation may explain why the calculated concentration of released PT does not match with the observed loss of prochelator.

FIG. 2: UV chromatography shows conversion of DB4-51 by β-lactamase. LC-MS performed on samples containing 100 μM DB4-51, 10 μM Rofecoxib (as internal standard), and 0.5 units/mL β-lactamase in PBS. Samples were incubated at room temperature and analyzed via LC-MS at time 0. The mass spectrum corresponding to the chromatographic peak eluting at 14 min matches the expected m/z value for DB4-5. After incubation, a new peak appears at 7 mins with corresponding m/z values consistent with expected masses of PT disulfide and the 2:1 PT complex with iron. The internal standard was Rofecoxib which elutes at 16 min. The concentrations of DB4-51, PT, and internal standard were calculated based on prepared calibration curves of the integrated area under the UV peak of each component.

The stability of the prochelator in cultures of ampicillin-resistant and susceptible bacteria was monitored by LC-MS in order to correlate the activity of the prochelator with the degree of β-lactamase-catalyzed release of PT. Indeed, the concentration of intact DB4-51 after 4 hours of incubation in a culture of UTI89 *E. coli* was found to be nearly 80% of the starting concentration (F), whereas less than 10% was detectable from samples incubated with the ampicillin-resistant ESBL *E. coli* strain. The IC$_{50}$ values of DB4-51 in these two *E. coli* strains, UTI89 and ESBL are 27 and 8 respectively. Klebs isolates 4 and 9 (FIG. 3) also showed a difference in recoverable prochelator that correlates with efficacy. Whereas 90% of DB4-51 remained intact after 4 hours with isolate 4 (IC$_{50}$=133 μM), less than 15% was found for Klebs isolate 9, for which the IC$_{50}$ is only 10 μM. The correlation between IC$_{50}$ and prochelator conversion supports the hypothesis that strains with high β-lactamase activity will be most susceptible to attack by our prochelator strategy.

Figure 3:
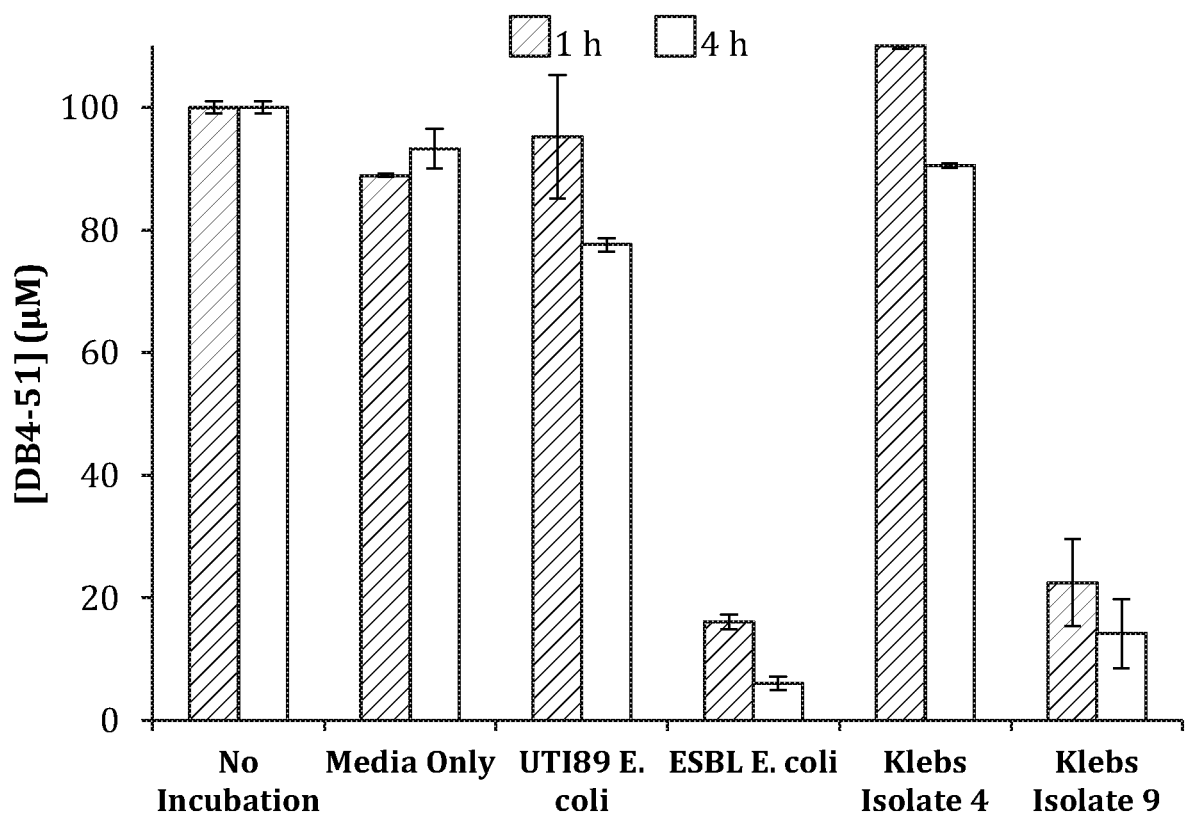
FIG. 3 shows the Disappearance of detectable DB4-51 remaining in bacterial cultures correlates with antimicrobial activity. The concentration of intact DB4-51 was quantified by an LC-MS assay after 100 μM treatments of DB4-51 were incubated for 1 and 4 h in LB media only or in LB cultures of UTI89 $E.$ $coli$, ESBL $E.$ $coli$, and $K.$ $pneumoniae$ isolates 4 and 9. All samples were prepared in triplicate and the error bars represent the standard deviation about the mean of those samples. ESBL $E.$ $coli$ and Klebs isolate 9 have $IC_{50}$ values for DB4-51 of 8 and 10 μM, whereas the values for UTI89 and isolate 4 are 27 and 133 respectively.

FIG. 3: Disappearance of detectable DB4-51 remaining in bacterial cultures correlates with antimicrobial activity. The concentration of intact DB4-51 was quantified by an LC-MS assay after 100 μM treatments of DB4-51 were incubated for 1 and 4 h in LB media only or in LB cultures of UTI89 *E. coli*, ESBL *E. coli*, and *K. pneumoniae* isolates 4 and 9. All samples were prepared in triplicate and the error bars represent the standard deviation about the mean of those samples. ESBL *E. coli* and Klebs isolate 9 have $IC_{50}$ values for DB4-51 of 8 and 10 μM, whereas the values for UTI89 and isolate 4 are 27 and 133 μM, respectively.

Figure 4:
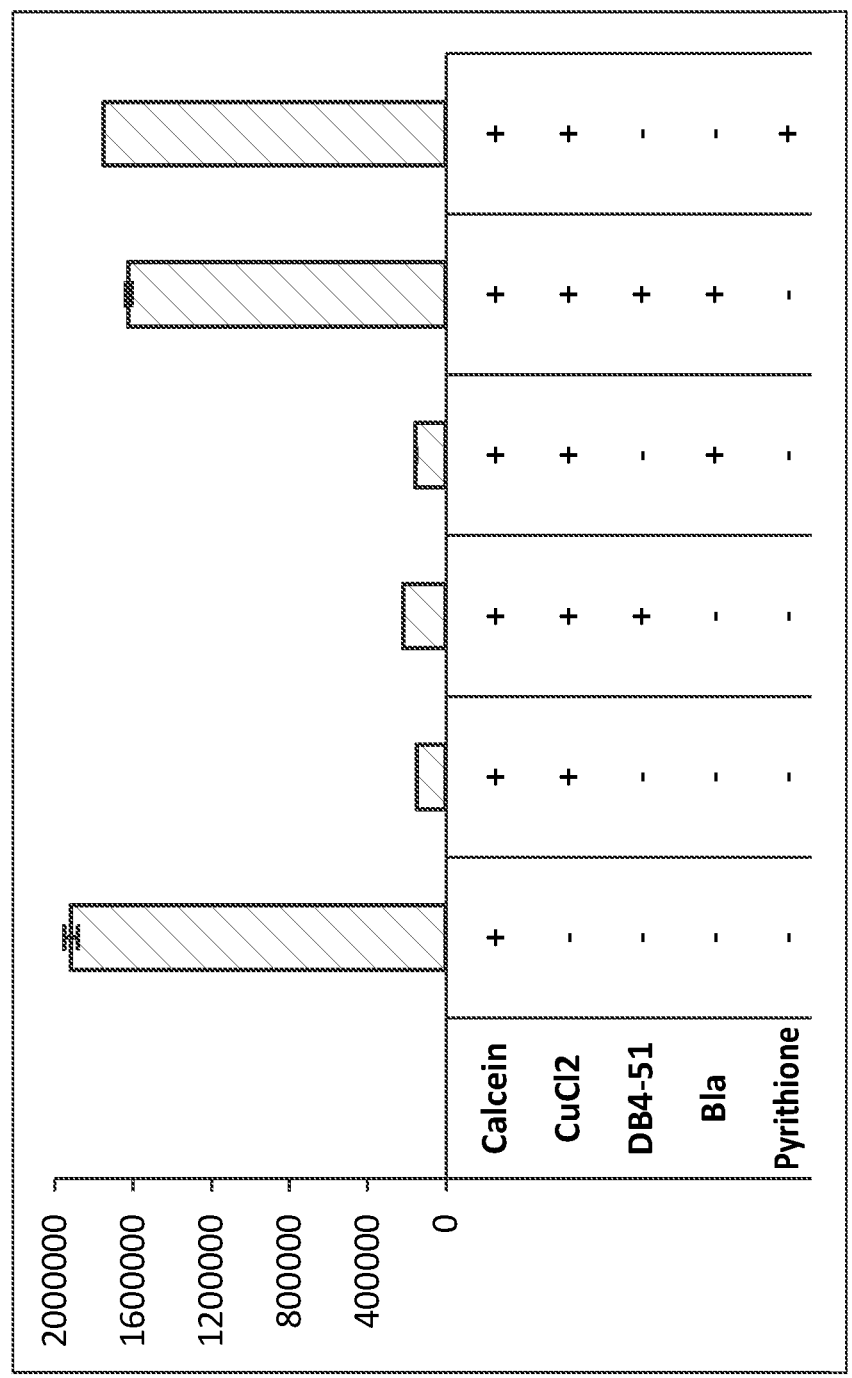
FIG. 4 is a calcein fluorescence assay showing the release of pyrithione in the presence of β-lactamase.

A calcein fluorescence assay for metal competition was utilized in order to evaluate the relative metal-binding affinity of DB4-51 compared to PT. The fluorescence intensity of the probe calcein is quenched by more than 90% upon binding $Cu^{2+}$. As shown in FIG. 4, addition of PT to Cu-loaded calcein restores calcein fluorescence, whereas DB4-51 does not compete with calcein for Cu binding. However, when incubated with 10 equivalents of DB4-51 and 0.1 units/mL Type III β-lactamase from *Enterobacter cloacae*, there is an 85% return in calcein fluorescence, which correlates well with the 90% return observed for PT itself at the same concentration. This experiment confirms that the minimal affinity of the prochelator for Cu can be dramatically increased upon exposure to β-lactamase.

FIG. 4: Relative Cu binding assay with DB4-51 and PT against calcein. Solutions of 2 μM calcein and 2.4 μM $CuCl_2$ in pH 7.4 PBS were equilibrated at room temperature for 2 hours prior to addition of 20 μM PT, 20 μM DB4-51, and/or 0.1 units/mL β-lactamase (Bla). Fluorescence emission at 535 nm ($\lambda_{ex}$=485 nm) was recorded after one hour. Error bars represent the standard deviation about the mean.

Figure 5:
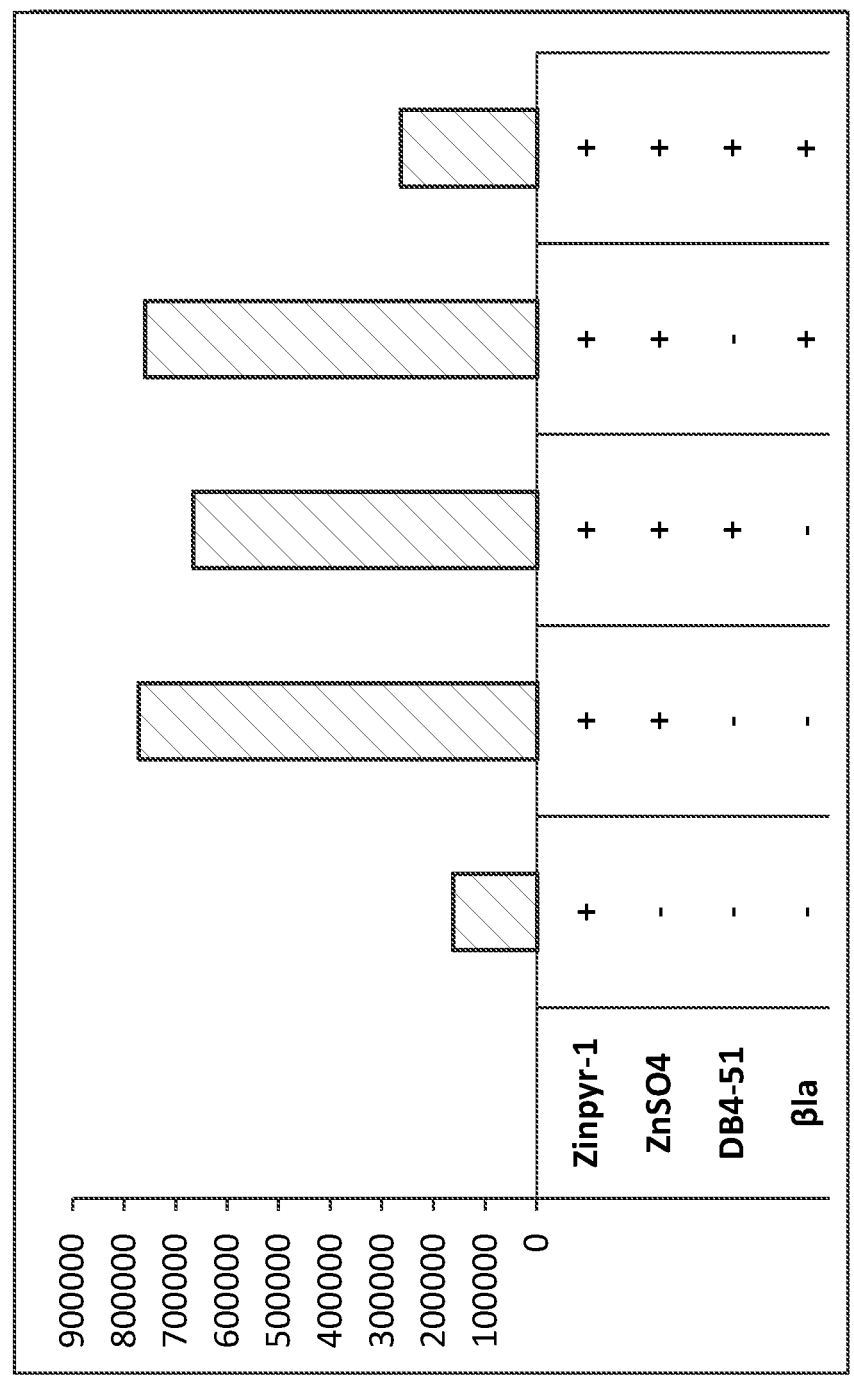
FIG. 5 is a Zinpyr-1 fluorescence assay showing the release of pyrithione in the presence of β-lactamase.

The fluorescent probe zinpyr-1 has affinity for Zn2+ and, upon binding, exhibits a fluorescence increase. FIG. 5 shows that the addition of Zn2+ to zinpyr-1 causes a fluorescence increase that is unaffected by addition of 400 equivalents of DB4-51. However, immediately upon β-lactamase addition, the fluorescence decreases by more than 50%, indicating that pyrithione has been released and is removing Zn2+ from zinpyr-1.

FIG. 5: Zinpyr-1 fluorescence assay shows the release of pyrithione in the presence of β-lactamase. Zinpyr-1 was excited at 485 nm and the emission was recorded at 535 nm. Lane one shows the fluorescence of 0.25 μM zinpyr-1 in PBS while lane two shows the dramatic fluorescence increase that takes place when four equivalents of $ZnSO_4$ are added to the solution. Lanes three and four contain 100 μM DB4-51 and 0.5 units/ml β-lactamase respectively and confirm these molecules are innocent in the fluorescence of zinpyr-1. Lane five contains 100 μM DB4-51 and 0.5 units/ml β-lactamase.

5.4.3. Prochelator Efficacy is Modulated by Copper Availability

The mechanism of action of PT has been reported to relate to its ionophoric activity that enables it to elevate intracellular Cu to toxic levels. [39, 40] We therefore reasoned that bacterial growth inhibition by PT and DB4-51 might be attenuated by manipulating the availability of Cu in the growth medium. To control for the impact of copper alone, the cultures of 5 bacterial strains were subjected to a serial dilution of $CuCl_2$. At concentrations up to 500 μM, $CuCl_2$ reduced the growth of UTI89, MRSA, and Klebs cultures by less than 20%. In contrast, the growth of both strains of K-12 *E. coli* increased 5-20% in media containing 10 μM supplemental $CuCl_2$. This observation is consistent with reported results that up to 750 μM supplemental Cu can increase the growth of K-12 *E. coli*. [41] To control for the impact of limited Cu, several strains were also challenged with a serial dilution of BCS. Treatment with BCS did not inhibit bacterial growth at concentrations below 1 mM. Combined, these control experiments show that these bacterial strains are remarkably adept at growing under conditions of both Cu excess and Cu limitation.

To control for any influence that extracellular Cu levels may have generally on the response to an antibiotic, dose-response curves of wild type K-12 and ampicillin-resistant K-12+Bla *E. coli* were generated against ampicillin under Cu-replete (10 μM $CuCl_2$) and Cu-limiting (500 μM BCS) conditions. Neither condition caused any significant change in the $IC_{50}$ of the susceptible strain. Likewise, the $IC_{50}$ of ampicillin in the +Bla (resistant) strain was unaffected by Cu status and remained greater than 250 μM regardless of condition. These controls suggest that any impact of Cu availability on the $IC_{50}$ value of test compounds may indicate a dependence on Cu unique to that molecule.

The $IC_{50}$ values of PT in combination with 10 μM supplemental Cu either remained very similar to those of PT alone (Klebs and MRSA), or up to 2-fold elevated (all strains of K-12 and UTI89 *E. coli*) (Table 2). Given that K-12 *E. coli* showed robust growth in the presence of supplemental Cu, it is possible that supplemental Cu improves the overall fitness of the bacteria in a way that improves their defense against stress imposed by PT. Such a response seems counterintuitive given the Cu-dependent mechanism of action associated with PT. The 2:1 complex of PT with $Cu^{2+}$ is poorly soluble in aqueous solution, so an alternative hypothesis is that addition of excess Cu favors complex formation and precipitation, which could lower the effective concentration and manifest as an increase in $IC_{50}$. While no precipitation was obvious, this possibility cannot be ruled out.

Compared to the Cu-replete conditions, more substantial increases in the $IC_{50}$ of PT are observed across all strains tested under the Cu-limiting conditions imposed by co-incubation with 500 μM BCS. The diminished activity of PT under these conditions is consistent with the premise that its mechanism of action involves interaction with Cu. However, even under Cu limiting conditions, PT maintains $IC_{50}$ values in the 6-20 μM range, depending on strain (Table 2). This observation suggests either that these conditions are not sufficiently Cu-deficient to abrogate activity or that PT activity has additional mechanisms of action that are independent of Cu.

As was the case with PT, prochelator DB4-51 also showed only modest if any improvements in $IC_{50}$ value as a function of 10 μM supplemental Cu for most strains (Table 2). The remarkable exceptions to this trend are the response of ESBL *E. coli* and MRSA to DB4-51 under Cu-replete conditions. In the case of MRSA, the $IC_{50}$ improves from 10 to 0.4 μM upon Cu supplementation. This improvement in efficacy for the prochelator is particularly interesting because it is significantly better than the chelator PT itself, for which the $IC_{50}$ decreases from 11 to 7 μM upon Cu supplementation. In contrast, ESBL *E. coli* is somewhat less sensitive to DB4-51 in the presence of 10 μM supplemental Cu (the $IC_{50}$ increases from a mean of 8 to 20 μM with supplemental Cu). The fact that changing the Cu concentration in the media can influence the potency of DB4-51 may stem from the different biological systems that are responsible for antibiotic resistance in these bacteria. For example, upregulation of efflux pumps in ESBL *E. coli* may be responsible for removing the prochelator before a sufficient portion of PT has been released.

The synergy of DB4-51 with Cu is most pronounced for MRSA grown under Cu-limiting conditions, for which the $IC_{50}$ increases above 20 µM. The swing in efficacy of DB4-51 against MRSA under Cu-replete (0.4 µM) vs. Cu-limited (22 µM) conditions represents a 55-fold change in $IC_{50}$ value as a function of Cu availability. *E. coli* UTI89 expressing plasmid-based β-lactamase (pCOM-GFP) showed a 10-fold change in $IC_{50}$ value depending on Cu status, going from 8 to 80 µM for Cu replete vs Cu depleted conditions, respectively, while +Bla K-12 *E. coli* showed less than 4-fold change.

Further evidence for the influence of bioavailable copper on the $IC_{50}$ of DB4-51 was obtained by using a checkerboard assay. The checkerboard assay is useful for visualizing the synergistic or antagonistic activity of two compounds by titrating one compound on each perpendicular axis of a 96-well plate and monitoring the $OD_{600}$ of the wells as an indicator of bacterial growth. Serial dilutions of DB4-51 in LB were arrayed against dilutions of chelator (BCS and EDTA). The antagonism exists between our prochelator, DB4-51, and the strong, extracellular chelators BCS and EDTA. For example, at 52 µM DB4-51, more than twice its $IC_{50}$, titrating 125 µM or more of the Cu-chelator BCS into the media restored *E. coli* growth. At high concentrations (>125 µM) of the metal chelator EDTA there is some inhibition of bacterial growth, presumable due to metal nutrient withholding. However, at lower concentrations, EDTA works antagonistically with DB4-51 by restoring bacterial growth. This trend further underscores the influence that copper and potentially other metals have on the growth inhibitory activity of DB4-51.

5.4.4. Effect of DB4-51 on Total Cellular Metal Content

PT is recognized as an ionophore that shuttles metals across cell membranes and thereby disrupts cellular metal homeostasis. The observations that extracellular metal chelators abrogate the efficacy of DB4-51 suggest that PT released by activation of DB4-51 may influence the metal content of treated cells. To test this hypothesis, inductively-coupled plasma mass spectrometry (ICP-MS) was used to measure the concentration of cell-associated copper, iron, and zinc for +Bla K-12 *E. coli* grown under a variety of conditions. Untreated *E. coli* grown in LB media were compared to those incubated for one hour in LB containing 0, 2.5, 5, or 10 µM DB4-51 or PT with and without 10 µM supplemental $CuCl_2$. The concentrations of cell-associated metals in +Bla *E. coli* grown in these conditions are reported as a ratio against bacterial growth as measured by the $OD_{600}$ reading at the time of sampling.

Figure 6:
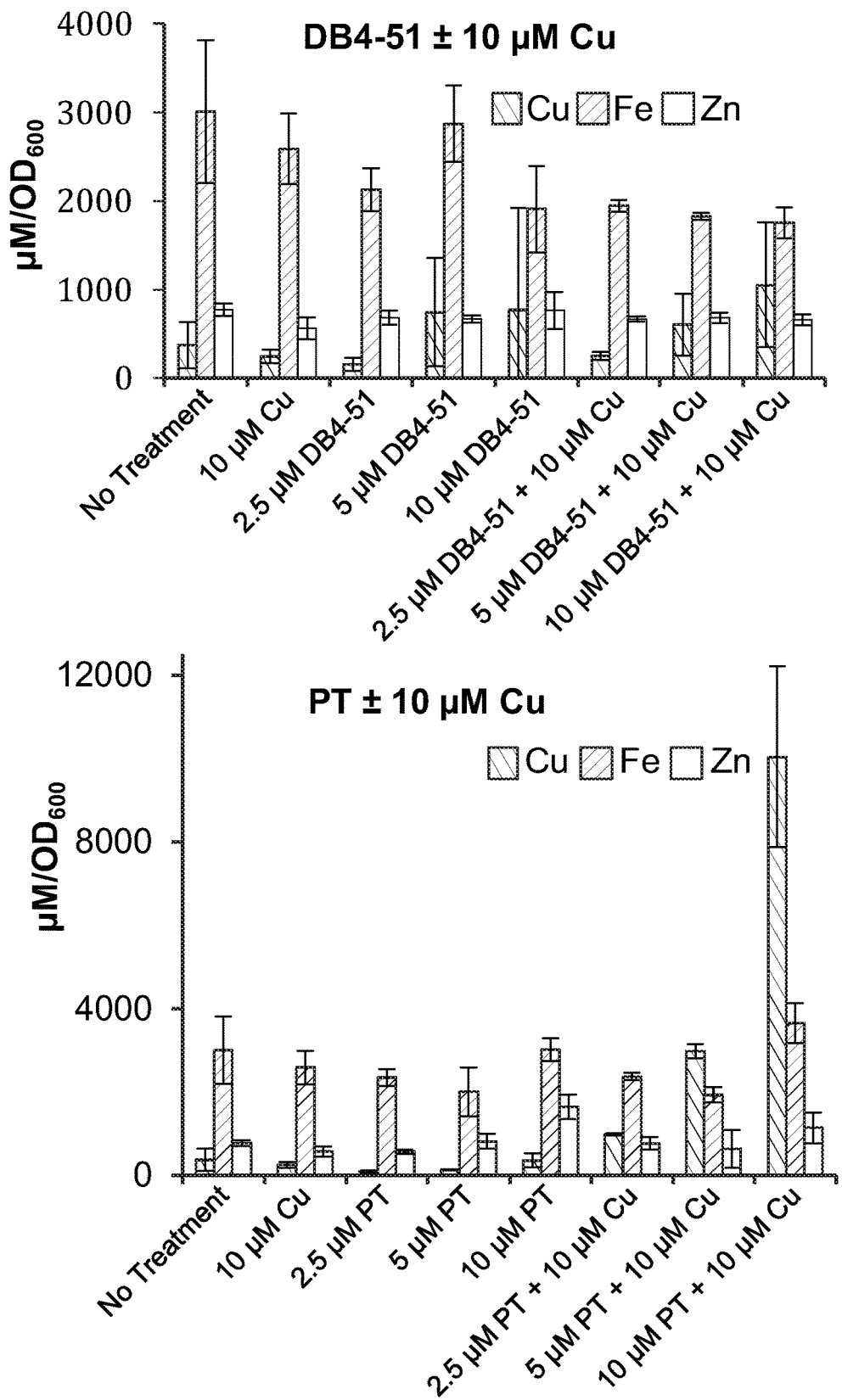
FIG. 6 shows the cellular metal concentrations of +Bla K-12 $E.$ $coli$.

As shown in FIG. 6, there were no significant changes in cell-associated copper, iron, or zinc in *E. coli* incubated in LB containing 10 µM supplemental $CuCl_2$, 2.5-10 µM PT, or 2.5-10 µM DB4-51, compared to the untreated control. However, incubating PT with 10 µM supplemental $CuCl_2$ showed a dose-dependent increase in cell-associated copper, resulting in a 30-fold increase over the $CuCl_2$ control for the maximal PT dose. In comparison, co-incubation of 10 µM DB4-51 and 10 µM supplemental $CuCl_2$ resulted in a slight but statistically insignificant increase in cell-associated copper compared to the supplemental $CuCl_2$ control.

The difference in cell-associated Cu being high for PT+Cu and low for both PT alone and DB4-51+Cu does not correlate with growth inhibitory efficacy, as both compounds have $IC_{50}$ values around 14 µM under the +Cu condition, and even lower for PT alone (Table 2). While the high Cu result confirms that PT indeed functions as a Cu ionophore that concentrates Cu from the growth medium into cells, the fact that metal levels remained constant for the PT-only treatments suggests that hyperaccumulation of Cu is not explicitly required for the growth-inhibitory activity of PT. The metal content analysis combined with the checkerboard growth inhibition results therefore suggests a model in which PT released in situ from DB4-51 does not concentrate extracellular Cu from the growth medium into the cell, but rather likely acts on metals present within the periplasm. As the periplasm plays an important role in bacterial copper tolerance and resistance in Gram-negative bacteria, [42, 43] PT released within this space may interfere with bacterial responses to metal stress encountered in the host environment.

FIG. 6: Cellular metal concentrations of +Bla K-12 *E. coli*. Cultures of +Bla K-12 *E. coli* were incubated for 1 h in LB media, LB containing no treatment, 10 µM added $CuCl_2$, and DB4-51 (top) or PT (bottom) at indicated concentrations in the absence or presence of 10 µM $CuCl_2$. Metal contents of cell pellets were analysed via ICP-MS and reported as a function of $OD_{600}$. All treatments were performed in triplicate and the error bars represent the standard deviation about the mean.

5.4.5. Determination of IC50 Values for K-12 *E. coli*

In order to determine the antibiotic activity of DB4-51, a debilitated strain of *Escherichia coli* (HB101 K-12) was transformed with the pGLO plasmid from Bio-Rad in order to express β-lactamase. This transformation was confirmed by growing on a selective medium containing 100 µg/ml ampicillin in Lennox LB with 1.5% agar. A broth microdilution assay was employed to determine the relative activity of DB4-51 against susceptible (HB 101 K-12, no β-lactamase) and resistant (HB 101 K-12 transformed to express β-lactamase) *E. coli*. Using Lennox LB as the medium. serial dilutions of the test compounds were performed in a 96-well plate and then inoculated with *E. coli* before incubating for 16-20 hours at 35° C. The bacterial growth was monitored by recording each well's absorbance at 600 nm ($OD_{600}$.) The $OD_{600}$ values of *E. coli* suspensions incubated with various compounds were compared in order to assess their activities.

Figure 7:
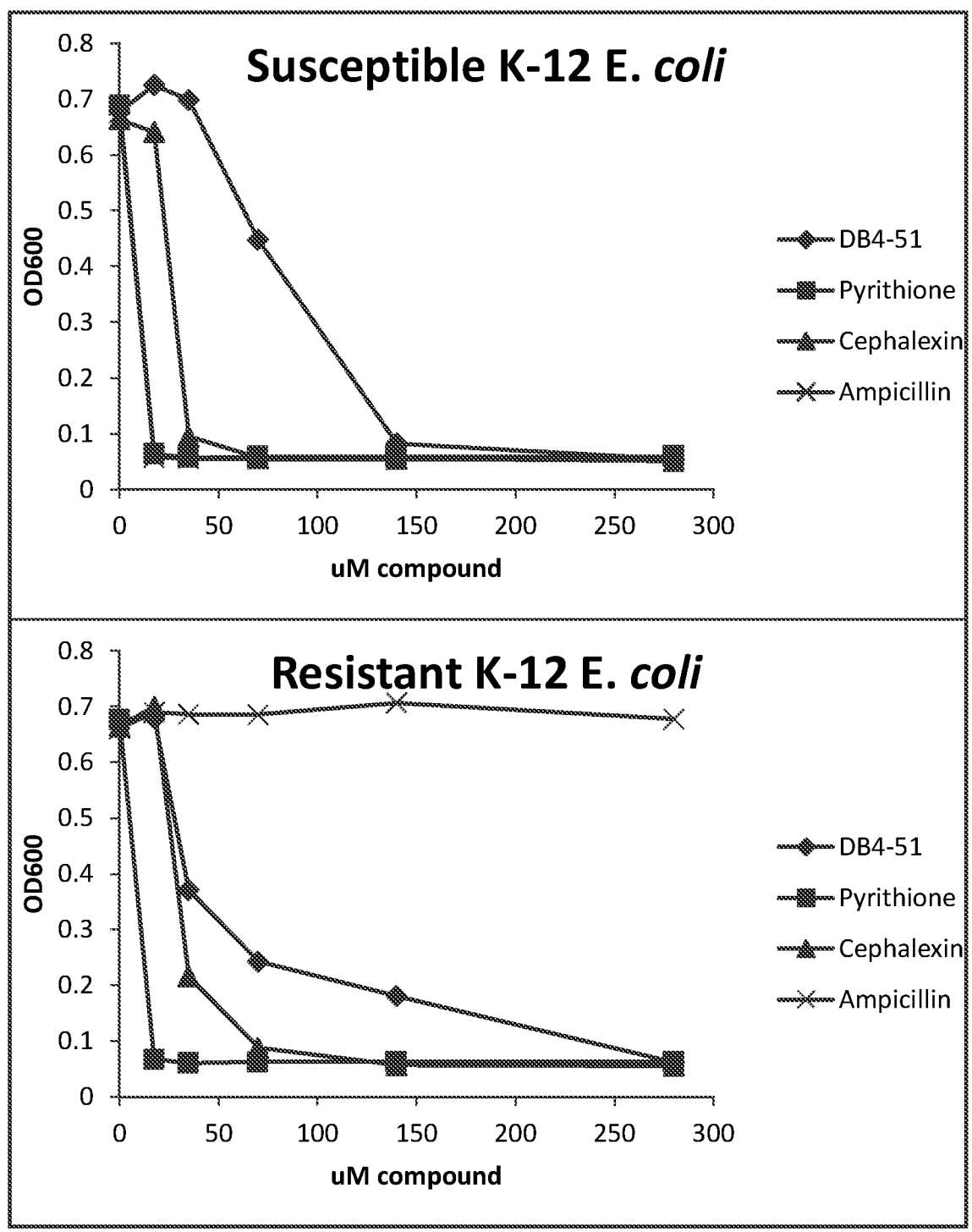
FIG. 7 are graphs showing $OD_{600}$ of susceptible and resistance K-12 $E.$ $coli$ cultures against DB4-51 and known antibiotics as a function of concentration.

As seen in FIG. 7, the penicillin-based antibiotic ampicillin is very active against the susceptible strain of *E. coli* while the cephalosporin-based compounds DB4-51 and cephalexin are only active above 17.5 µM.

FIG. 7: $OD_{600}$ of susceptible and resistant K-12 *E. coli* cultures against DB4-51 and known antibiotics as a function of concentration. Ampicillin has a penicillin core and cephalexin has a cephalosporin core. Cultures were grown in LB broth at 37° C. while shaking at 200 rpm for 18 hours and then diluted to an $OD_{600}$ of 0.005 before adding the compounds. Plates were grown at 35° C. while shaking at 200 rpm and the $OD_{600}$ was recorded after 18 hours.

As designed, the antibiotic activity of DB4-51 increases against the resistant strain of K-12 while the activity of cephalexin decreases slightly and ampicillin decreases dramatically. This result suggests that the presence of β-lactamase reduces the stability of the β-lactam and abolishes ampicillin's antibiotic activity entirely. The cephalosporin appears to be slightly more resistant to hydrolysis. This is evident by the fact that, although they are both built around the cephalosporin core, cephalexin has little response to β-lactamase while DB4-51 demonstrates enhanced antibiotic activity without reaching the activity of pyrithione. This trend can be seen in the preliminary results shown Table 1.

| IC$_{50}$ (μM) | | |
|---|---|---|
| | Susceptable | Resistant |
| DB4-51 | 80 | 39 |
| Cephalexin | 26 | 33 |
| Ampicillin | <18 | >560 |
| Pyrithione | <18 | <18 |

Table 1: Calculated IC50 values for DB4-51, cephalexin, ampicillin, and pyrithione. These values were derived by fitting the data to a log dose-response curve and reporting the concentration corresponding to half the maximum OD$_{600}$ value for each compound.

Figure 8:
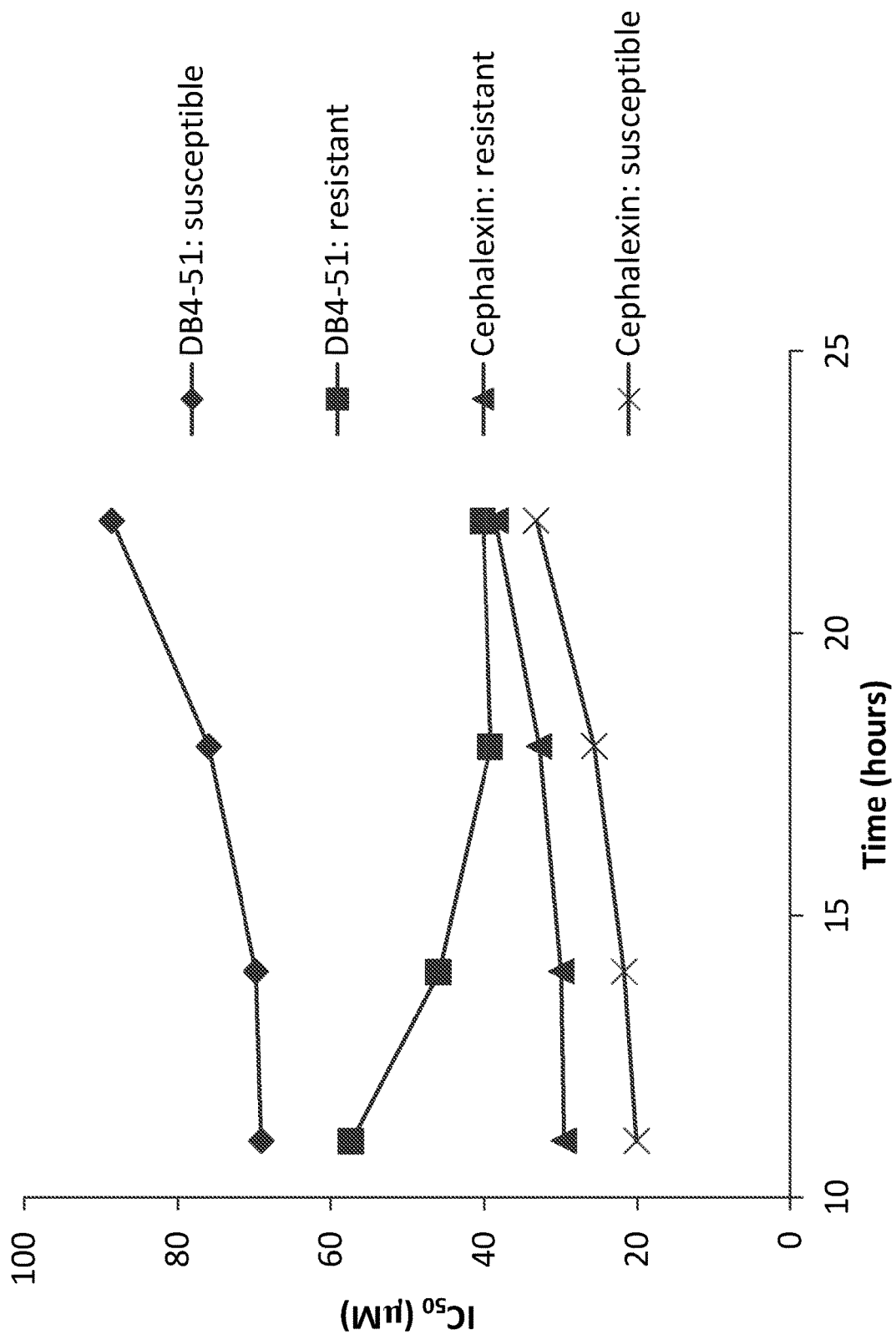
FIG. 8 is a graph showing the $IC_{50}$ of DB4-51 and cephalexin over time.

The level of inhibition of resistant K-12 that results from a single dose of DB4-51 or cephalexin depends on the incubation time, since surviving bacteria recover from the initial dose over time. As shown in FIG. 8, the IC50 value of cephalexin increases over time, presumably because the β-lactam inhibitor is slowly used up by irreversibly binding to DD-transpeptidase. Like cephalexin, the IC50 of DB4-51 increases for susceptible K-12 over time. However, the IC50 of DB4-51 for resistant K-12 decreases by 50% over 22 hours. This effect may be explained by the enzymatic hydrolysis of DB4-51 and subsequent release of pyrithione being slower than the hydrolysis of cephalexin. Once released, pyrithione persists in solution where it continues to inhibit growth as opposed to cephalexin which, once hydrolyzed, can no longer inhibit bulk growth.

FIG. 8. The IC50 of DB4-51 and cephalexin over time. Over time both resistant and susceptible K-12 are able to recover slightly from cephalexin as it is hydrolyzed. This trend is also observed for DB4-51 with susceptible K-12. Against resistant K-12 the IC50 is reduced by half.

The stability of the prochelator in cultures of ampicillin-resistant and susceptible bacteria was monitored by LC-MS in order to correlate the activity of the prochelator with the degree of β-lactamase-catalyzed release of PT. Indeed, the concentration of intact DB4-51 after 4 hours of incubation in a culture of UTI89 *E. coli* was found to be nearly 80% of the starting concentration, whereas less than 10% was detectable from samples incubated with the ampicillin-resistant ESBL *E. coli* strain. The IC$_{50}$ values of DB4-51 in these two *E. coli* strains, UTI89 and ESBL are 27 and 8 μM, respectively.

The assay was optimized and a summary of results are shown in Table 2. Specifically, Table 2 lists the IC$_{50}$ values (the concentration that results in half of the maximum growth inhibition of a bacterial culture) of DB4-51 against 7 bacterial strains compared to those of PT and ampicillin. As expected based on its known antimicrobial properties, PT inhibited bacterial growth across all strains tested, regardless of their susceptibility to ampicillin. Small variations in IC$_{50}$ from 2-11 μM indicate only slight differences in species- and strain-specific susceptibility to PT. While not as effective as ampicillin, DB4-51 does display some inhibitory activity against the ampicillin-susceptible *E. coli* non-pathogenic HB101 and pathogenic UTI89, with median IC$_{50}$ values of 18 and 27 μM, respectively. This result suggests that the cephalosporin conjugate retains some traditional β-lactam activity in the presence of bacteria that do not express β-lactamase.

TABLE 2

IC$_{50}$ values of ampicillin, PT, and DB4-51 with and without copper. IC$_{50}$ values of DB4-51 in LB broth, LB supplemented with 10 μM CuCl$_2$, or LB supplemented with 500 μM BCS, a Cu chelator. Tested strains include −Bla K-12 *E. coli*, +Bla K-12 *E. coli*, UTI89 *E. coli*, pCOM *E. coli*, ESBL *E. coli*, *Klebsiella pneumonia* (Klebs), and Methicillin-Resistant *Staphylococcus aureus* (MRSA). 95% confidence intervals are in parentheses.

| Strain | IC$_{50}$ (nM) (95% confidence interval) | | | | | | |
|---|---|---|---|---|---|---|---|
| | Ampicillin | PT | DB4-51 | PT + Cu | DB4-51 + Cu | PT + BCS | DB4-51 + BCS |
| −Bla K-12 *E. coli* | 8 (7.2-8.9) | 7 (5.6-8.8) | 18 (16.4-20.2) | 12 (8.8-15.3) | 15 (13.7-16.3) | 19 (13.8-24.9) | 38 (31.9-44.8) |
| +Bla K-12 *E. coli* | >250 | 6 (5.9-6.4) | 14.5 (14.2-14.9) | 14 (11.6-16.4) | 14 (12.1-15.5) | 19 (10.9-32.1) | 51 (44.4-58.7) |
| UTI89 *E. coli* | 3 (1.8-4.5) | 2 (1.9-2.5) | 27 (24.4-29.9) | 4 (4.1-4.3) | 21 (12.0-37.0) | 6 (5.7-6.3) | 17 (12.4-22.8) |
| pCOM *E. coli* | >250 | 2 (1.8-3.1) | 11 (10.0-11.3) | 4 (2.4-15.8) | 8 (7.1-9.2) | 7 (5.4-10.2) | 80 (68.8-92.2) |
| ESBL *E. coli* | >250 | 5 (3.0-7.9) | 8 (6.8-9.2) | N/A | 20 (19.3-21.3) | N/A | 17 (15.3-18.1) |
| Klebs | >250 | 11 (9.3-13.1) | 37 (33.2-41.9) | 9 (7.3-11.2) | 25 (19.4-33.0) | 19 (17.7-20.4) | 20 (17.8-22.5) |
| MRSA | >250 | 10.0 (8.2-13.0) | 10 (8.3-13.1) | 7 (4.2-12.4) | 0.4 (0.1-1.6) | 11 (9.3-13.3) | 22 (13.9-35.8) |

One of the striking results from the data in Table 2 is that DB4-51 is even more effective against strains engineered to express β-lactamase (15 and 11 μM for K-12+Bla and UTI89/pCOM), respectively). Furthermore, DB4-51 shows respectable growth inhibition IC$_{50}$ values against pathogenic, drug-resistant isolates, notably ESBL *E. coli* (8 μM), MRSA (10 μM), and Klebs (37 μM). Given the fact that these strains are all resistant to ampicillin, these results strongly support the premise that DB4-51 operates by a mechanism of action that differs from traditional β-lactam antibiotics. These data are also consistent with our hypothesis that the release and activity of the active agent requires β-lactamase activation.

We observed that in most cases of the ampicillin-resistant strains tested the IC$_{50}$ of DB4-51 is 2-5-fold higher than that of PT. This observation may suggest that the full efficacy of PT is not achieved by DB4-51 in these strains. The exception is MRSA, the one Gram-positive strain tested and the one against which the activities of the two compounds are essentially the same, ~10 μM. Gram-positive bacteria express β-lactamase into the extracellular space, thus prochelator activation likely occurs extracellularly in these cases, which may result in released PT acting similarly to PT added directly to the culture broth. On the other hand, Gram-negative bacteria express β-lactamase into the periplasm, so any prochelator-derived PT is likely released between the cell membranes from prochelator that has been imported into the target cell. The difference in inhibitory activity between Gram-negative and Gram-positive bacteria may therefore derive from the differences in membrane access, protein interaction, and metal concentrations in the periplasm compared to the extracellular environment.

To demonstrate that the location of PT release affects its inhibitory activity, DB4-51 was pre-incubated with β-lactamase before dosing the bacteria. The $IC_{50}$ of DB4-51 decreased from 18 to 9 μM in −Bla K-12 E. coli and from 14.5 to 8 μM in +Bla K-12 E. coli when the bacteria were pre-incubated with β-lactamase. There are no statistical differences in the $IC_{50}$ values of PT, DB4-51 pre-incubated with β-lactamase, and PT pre-incubated with β-lactamase in either strain. These results suggest that the prochelator is less effective at inhibiting bacterial growth than the chelator and that conversion of the prochelator in the periplasmic space of E. coli is less effective than exogenously released PT.

Of the strains listed in Table 2, Klebs was the least susceptible to DB4-51, with a median $IC_{50}$ value of 37 μM. This comparatively diminished activity suggests that this clinical isolate may have low β-lactamase activity, low uptake of the prochelator, or the presence of alternative resistance mechanisms. Reasoning that resistance profiles and β-lactamase activity will vary significantly across isolates, we assayed DB4-51 against a panel of resistant Klebs clinical isolates and compared its $IC_{50}$ value to PT as well as the antibiotics ampicillin and ceftriaxone.

We suspected that the isolates most inhibited by DB4-51 would be those capable of releasing PT via their β-lactamase activity and thus the isolates most resistant to β-lactam antibiotics. This hypothesis is supported by the correlation between high $IC_{50}$ values for ampicillin and low $IC_{50}$ values for DB4-51 in almost every Klebs isolate tested (Table 3). Conversely, the $IC_{50}$ values of ceftriaxone and PT are in the low μM range for almost every isolate tested, suggesting that DB4-51 behaves differently from both a traditional β-lactam antibiotic and the chelator PT (Table 3).

chelator PT were evaluated in CCD-19Lu human lung fibroblast cells and HepG2 human liver epithelial cells. Using a cytotoxicity assay, the viability of mammalian cells was monitored as a function of their membrane integrity.

Figure 9:
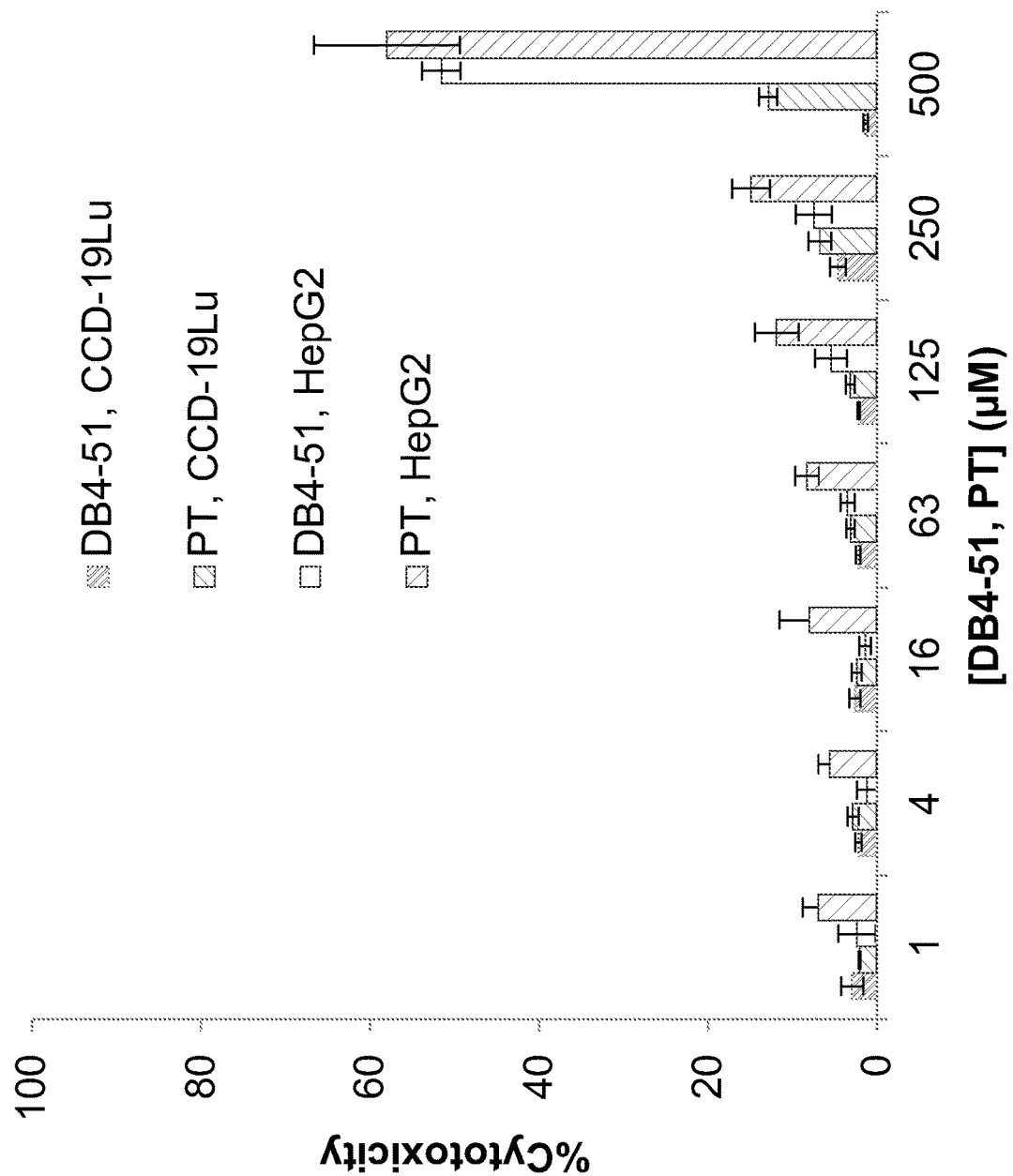
FIG. 9 shows the cytotoxicity of DB4-51 and PT in CCD-19Lu and HepG2 cells. Cytotoxicity of human lung fibroblast cells CCD-19Lu and human liver epithelial cells HepG2 was assessed with CellTox Green after 24 h incubation in serum-free LB medium containing noted concentrations of DB4-51 or PT. Error bars represent the standard deviation about the mean.

While the cytotoxicity of PT increases steadily with concentration, it does not induce more than 50% cell death at concentrations below 500 μM in either cell line after 24 hour incubation in LB (FIG. 9). DB4-51 shows even less cytotoxicity and appears non-toxic below 250 μM, although it does induce greater than 50% cell death at 500 μM in HepG2 liver cells. Suspecting that the cytotoxicity apparent at high concentrations of DB4-51 in the mammalian cells may be due to PT released by non-specific hydrolysis of DB4-51, we analyzed the spent cell culture medium used for the cytotoxicity assay by LC-MS and found 50-60% loss of detectable, intact prochelator compared to the non-incubated controls after 4 hours. While these observations suggest that these mammalian cells are capable of hydrolyzing DB4-51, this activity is less efficient than in β-lactamase producing bacteria (FIG. 8), and it does not negatively impact the $LD_{50}$ of the prochelator, which is high in both CCD-19Lu and HepG2 mammalian cell lines. The large differential between the $IC_{50}$ values of DB4-51 in pathogenic bacteria in the low-μM range (Table 2) and the $LD_{50}$ of DB4-51 being >500 μM in mammalian cells (FIG. 9) indicates a ratio of $LD_{50}$ to $IC_{50}$ favorable for further development of DB4-51 as an antibacterial agent.

5.5. Prochelator Db4-162

5.5.1. Conversion of DB4-162 to TAT Requires β-Lactamase//Prochelator DB4-162 is Moderately Stable in Aqueous Media In order to monitor the stability of DB4-162, the absorbance spectrum was recorded in PBS. The sample was incubated at 37° C. and the absorbance spectrum was recorded periodically. After 72 hours only very small spectral changes occurred. Additionally, the concentration of the

TABLE 3

$IC_{50}$ values of DB4-51, PT, ampicillin, and ceftriaxone in Klebs clinical isolates. $IC_{50}$ values were calculated via broth microdilution of 1-500 μM of each compound in LB broth. Thirteen clinical isolates of *Klebsiella pneumonia* (Klebs) were tested in triplicate and the 95% confidence intervals are in parentheses.

| Klebs Isolate | $IC_{50}$ (μM) (95% CI) | | | |
|---|---|---|---|---|
| | DB4-51 | PT | Ampicillin | Ceftriaxone |
| 1 | 25 (18.3-33.0) | 10 (7.1-13.7) | 142 (65.3-306.6) | 0.4 (0.2-0.9) |
| 2 | 45 (32.5-61.0) | 5 (4.7-5.3) | >500 | 0.7 (0.6-0.8) |
| 3 | 163 (79.9-331.4) | 21 (10.1-43.6) | 55 (36.7-82.0) | 2.0 (1.4-3.0) |
| 4 | 133 (108.0-163.7) | 9 (8.0-10.0) | >500 | 1.0 (0.4-3.0) |
| 5 | 49 (41.5-57.7) | 11 (9.2-12.4) | 175 (63.4-484.3) | 0.1 (0.1-0.4) |
| 6 | 47 (35.1-62.5) | 6 (5.3-7.0) | 118 (60.9-229.1) | 0.3 (0.05-1.4) |
| 7 | 9 (5.2-15.0) | 10 (6.1-17.1) | >500 | 0.3 (0.2-0.4) |
| 8 | 30 (24.3-37.5) | 10 (8.1-13.4) | >500 | 0.1 (0.05-0.3) |
| 9 | 10 (8.0-11.3) | 9 (8.0-9.8) | >500 | 73 (52.0-102.8) |
| 10 | 150 (53.3-422.6) | 5 (3.6-7.3) | >500 | 0.03 (0.002-0.3) |
| 11 | 34 (27.3-42.1) | 6.5 (6.1-6.8) | 251 (184.1-343.2) | 0.01 (0.0005-0.4) |
| 12 | 52 (44.3-61.2) | 8 (7.3-8.5) | 112 (91.7-135.5) | 0.1 (0.02-0.8) |
| 13 | >500 | 11 (9.4-12.4) | >500 | 1 (0.7-2.4) |

5.4.6. Evaluation of Host Vs. Pathogen Toxicity

As the basis of the prochelator strategy is to prevent systemic exposure to potentially harmful metal chelating agents, the toxicities of both the prochelator DB4-51 and the prochelator in solution was monitored by LC-MS. A calibration curve was prepared after a serial dilution of DB4-162 was analyzed on the instrument and the area under the broad absorbance band at 260-300 nm that correlates with the prochelator was integrated. This curve was then used to calculate the concentration of DB4-162 present in solution after incubating in PBS at 37° C. The sample was analyzed by LC-MS after 0, 24, and 72 hours. After incubating in PBS for 24 hours more than 85% of the original signal was still observed by LC-MS. However, after 72 hours, it was calculated that approximately 60% of DB4-162 was still present in solution. Given the lack of degradation products in the mass spectrum and the absence of any new absorbance peaks it is possible that aggregation of the prochelator over time is the cause of the observed loss of signal. Together, the UV-Vis and LC-MS data support the overall stability of DB4-162 in aqueous conditions. By comparison, the half-life of most β-lactam antibiotics in vivo is a few hours.[44, 45]

5.5.2. LC-MS Detection of β-Lactamase Reaction Products

Figure 10:
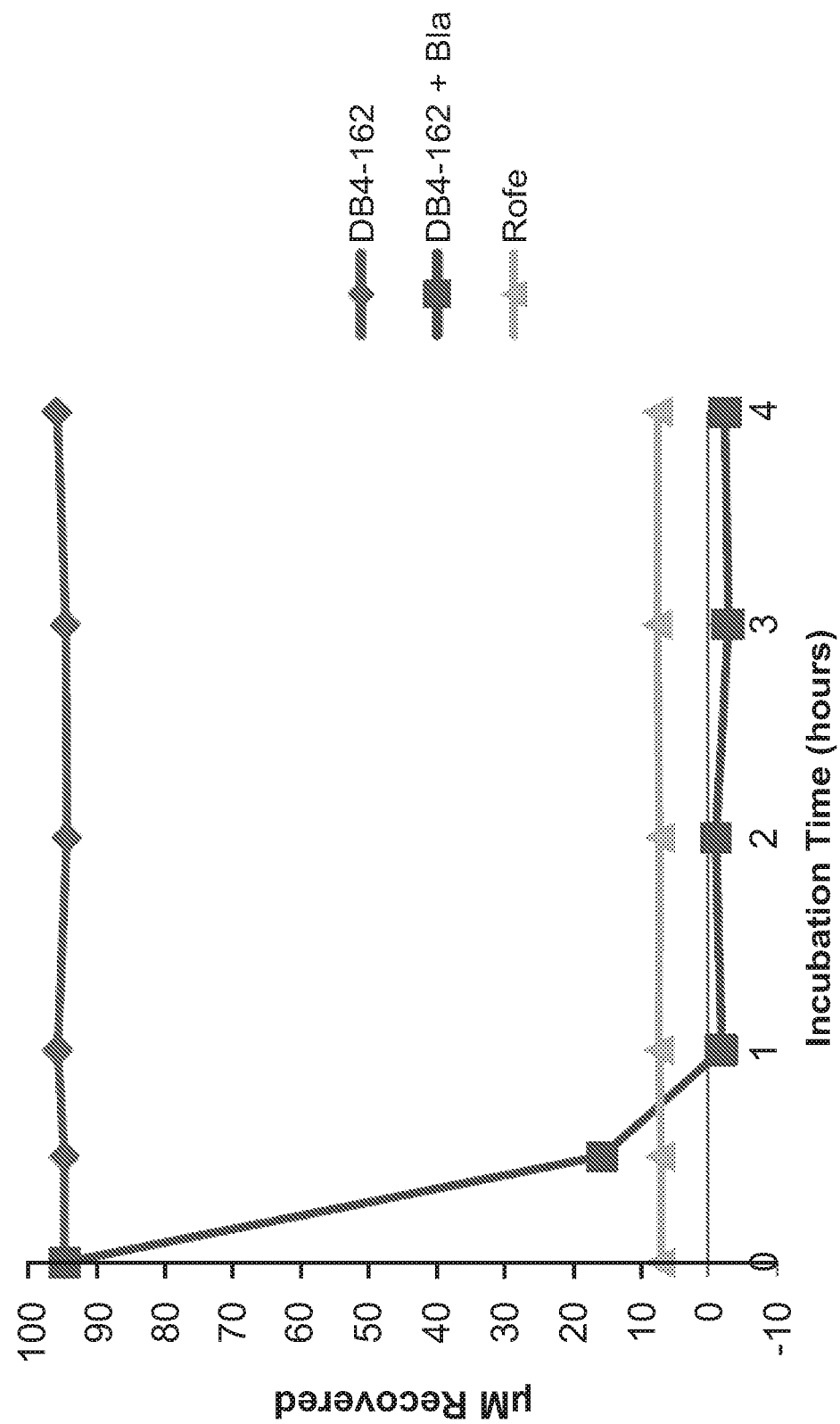
FIG. 10 shows the concentration of DB4-162 present by LC-MS after incubation with β-lactamase. The concentration of DB4-162 was calculated based on prepared calibration curves of the integrated area under the UV absorbance peak at 260-300 nm. Samples were incubated in pH 7.4 PBS for 0-4 hours in the presence and absence of 0.1 units/mL β-lactamase. Rofecoxib (Rofe) was added to the samples to serve as an internal standard.

The reaction products of the prochelator DB4-162 were analyzed by LC-MS. A sample of 100 μM DB4-162 and 10 μM Rofecoxib (internal standard) in PBS was divided into two LC-MS vials and to one was added 0.5 units/mL β-lactamase. After incubating at room temperature, the samples were run on the LC-MS. Integrating the area under the peak of the UV-trace gives a measure of the concentration of that species. By serial dilution, a calibration curve was constructed in order to quantify the concentration of DB4-162 present in solution. The mass spectrum confirms that the prochelator, with a molecular weight of 477.1 g/mol, elutes at 14.5 minutes (FIG. 10). Although the prochelator appears stable without the enzyme, after incubating with β-lactamase for 4 hours the prochelator peak is reduced by more than 95%.

The reduction of the prochelator peak at 14.5 minutes is concomitant with the appearance of a new peak that elutes at 6.3 minutes. The mass spectrum corresponding to the species eluting at 6.3 minutes gives the m/z values of 148.0, 293.0, and 348.0, consistent with the presence of TAT (147 g/mol), the disulfide form of TAT (293 g/mol) and the 2:1 complex with Fe3+(348 g/mol). The aforementioned complications in quantifying pyrithione are likely applicable to TAT thus the release of TAT cannot be accurately quantified chromatographically.

Figure 11:
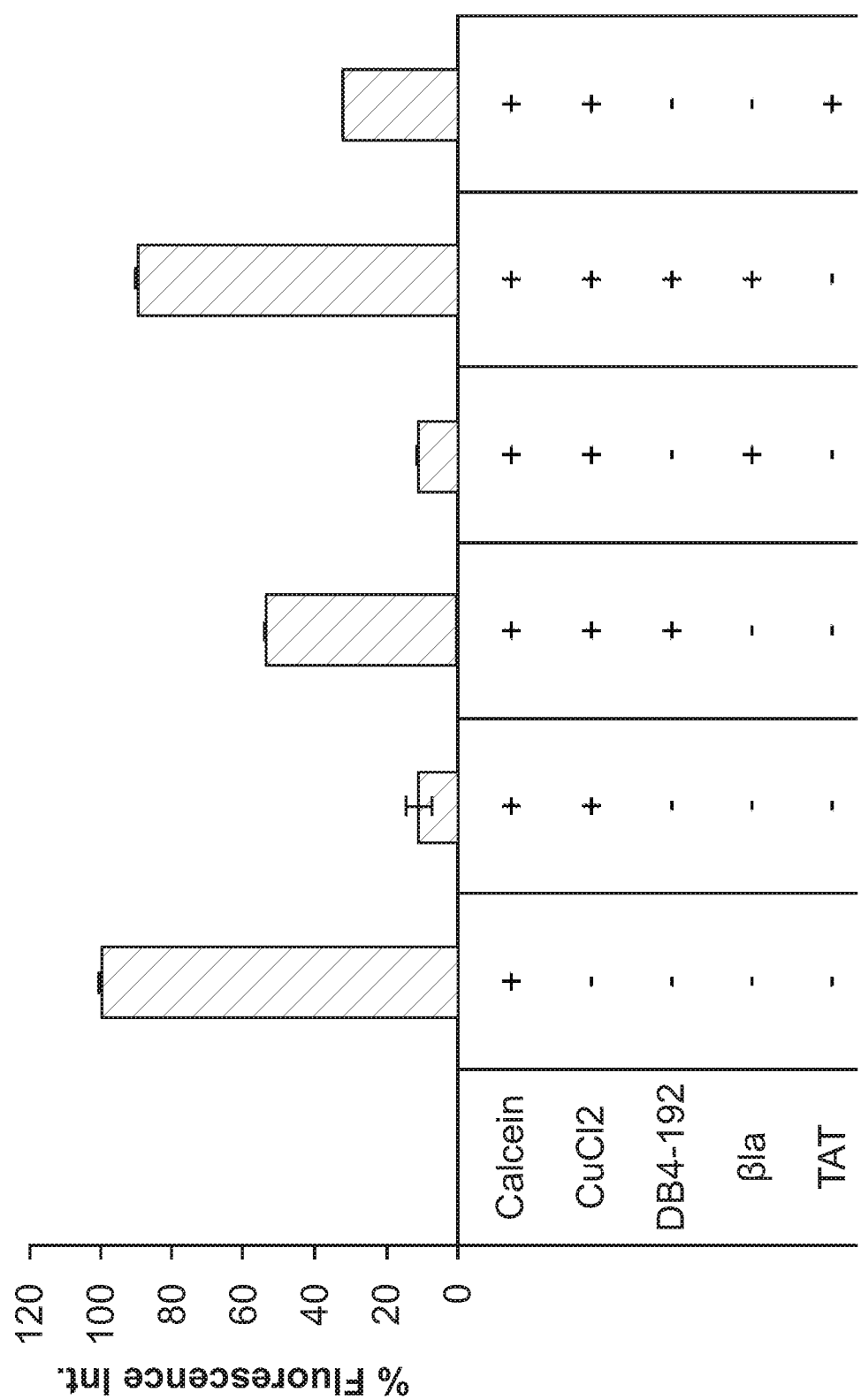
FIG. 11: To solutions of 2 μM calcein in pH 7.4 PBS was added 2.4 μM CuCl2 and the samples were fully equilibrated at room temperature for 2 hours. Next, 20 μM TAT, 20 μM DB4-162, 0.1 units/mL β-lactamase were added and the fluorescence at 500 nm was recorded after one hour. Error bars represent the standard deviation about the mean.

5.5.3. Calcein Fluorescence Assay Confirms Released TAT is an Active Chelator The calcein assay was utilized in order to assess the relative copper chelating ability of the prochelator and TAT. The fluorescence emission of calcein is quenched by more than 90% in the presence of 1.2 equivalents of CuCl2 (FIG. 11). Titration with TAT results in an increase in calcein fluorescence that is 30% recovered by 10 equivalents of TAT indicating that TAT is not able to readily out-compete calcein for Cu2+-binding. The addition of 0.1 units/mL β-lactamase alone has no effect on the quenched fluorescence signal of the Cu-calcein solution. Interestingly, the addition of 10 equivalents of DB4-162 restores approximately 50% of the original fluorescence of calcein. This fluorescence return indicates that, despite donor-atom masking, DB4-162 has some affinity for copper. However, when incubated with 10 equivalents of DB4-162 and 0.1 units/mL β-lactamase there is a 90% return in calcein fluorescence. This suggests that the prochelator effectively blocks metal binding activity until it is converted to the active form by β-lactamase. While it is unclear why 10 equivalents of TAT are insufficient to out-compete calcein for copper, it may be related to the propensity of TAT to form other species in aqueous media.

5.5.4. Screening DB4-162 Against Pathogenic Bacteria

The ability of DB4-162 to inhibit bacterial growth was assessed by a traditional broth microdilution method that assesses the turbidity of liquid cultures in the presence of varying concentrations of the compound. As described above for DB4-51, the antibacterial properties of the prochelator DB4-162 were assessed in non-pathogenic lab-strain HB101K-12 *E. coli* and compared to the pGLO-transfected mutant HB101K-12 *E. coli* that express β-lactamase. Clinically relevant pathogenic bacteria were also screened, including UTI89 *E. coli*, pCOM transfected UTI89 *E. coli* (pCOM), extended spectrum β-lactamase (ESBL) *E. coli*, methicillin-resistant *Staphylococcus aureus* (MRSA), and *Klebsiella pneumonia* (Klebs). In addition to being naturally resistant to many β-lactam antibiotics, MRSA can produce a number of β-lactamases. [46] The exact mechanisms of resistance for the ESBL and Klebs clinical isolates used here are unknown; however they were screened against clinical antibiotics and were observed to be resistant to ampicillin. It should be noted that all of the bacteria tested are gram-negative except for gram-positive MRSA.

The goal of this screen was to calculate the IC50 of the prochelator in a series of pathogenic bacteria and compare these values to the IC50 of known antibiotics in those same strains to determine the relative effectiveness of DB4-162 against the drug-resistant and drug-susceptible bacteria in comparison to current antibiotic treatment options. Bacterial growth was monitored in LB broth at 37° C. in the presence and absence of DB4-162 for 20 hours. A concentration gradient of DB4-162 from 500 to 0 μM was used to screen all 7 strains of bacteria and the dose-response curves were fit to a linear regression to calculate the IC50 of DB4-162 in each strain. These IC50 values are an approximation of how effectively DB4-162 inhibits the growth of each bacterial strain in vitro. To determine if the antibiotic mechanism of action of DB4-162 is metal-dependent, the titration of DB4-162 was also performed in media containing 10 μM supplemental $CuCl_2$ or 500 μM bathocuproine disulfonate (BCS) which creates a Cu-deficient growth environment by sequestering extracellular copper in a high-affinity, membrane-impermeable Cu+-complex.

5.5.5. Testing DB4-162 in HB101K-12 *Escherichia coli*

Figure 12:
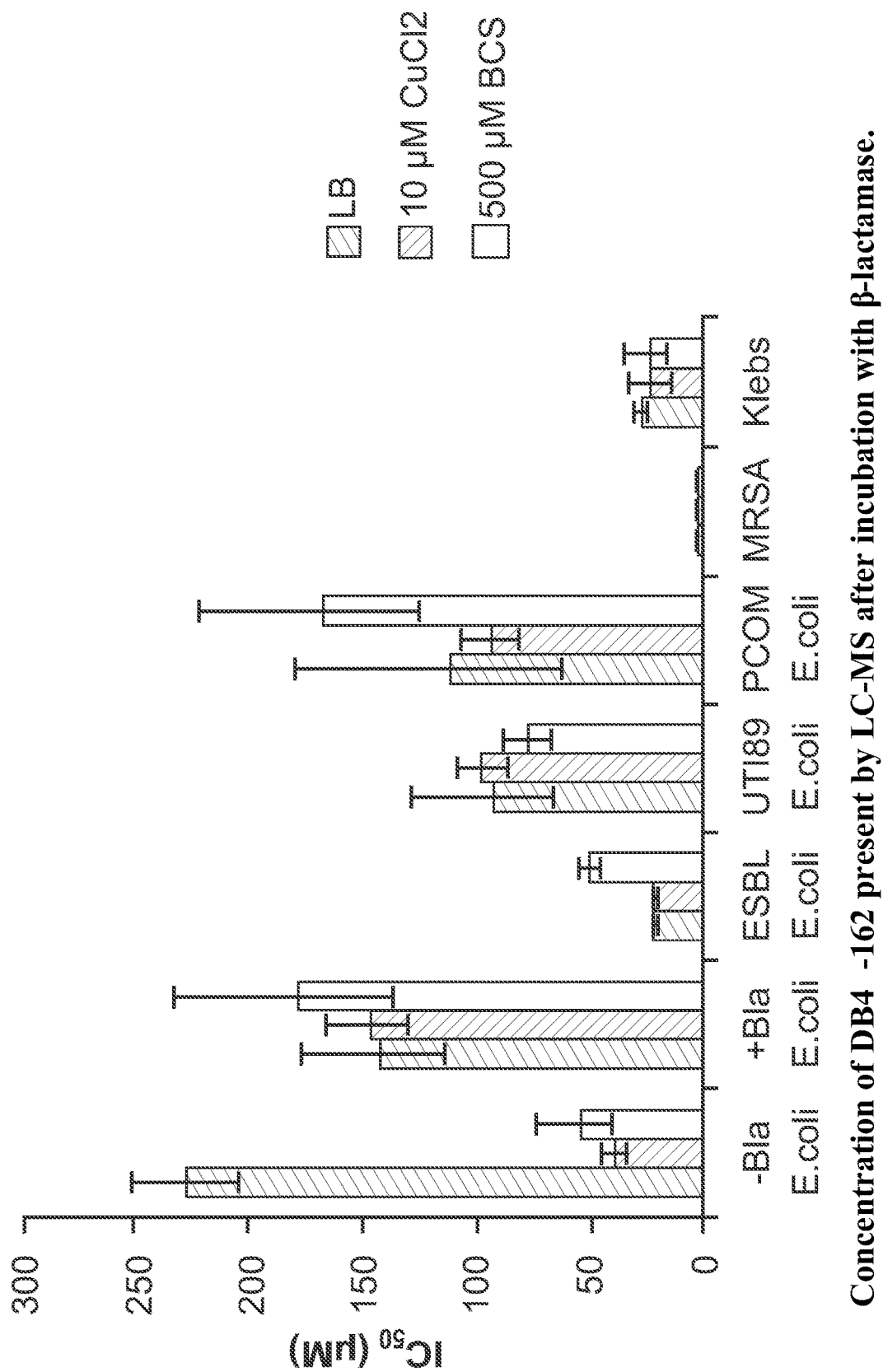
FIG. 12: IC50 values were calculated via broth microdilution of DB4-162 in LB broth, LB supplemented with 10 μM CuCl2, or LB supplemented with 500 μM BCS. Error bars represent the 95% confidence interval as from a variable slope, nonlinear regression fit to the dose-response $OD_{600}$ data.

The prochelator DB4-162 was screened against both the ampicillin-susceptible (−Bla) and resistant (+Bla) K-12 strains (FIG. 12). The IC50 of ampicillin for the −Bla and +Bla strains are 8 μM and >250 μM, respectively. DB4-162 was found to have a slightly lower IC50 (143 μM) in +Bla K-12 than in −Bla K-12 (227 μM) (Table 4). These IC50 values are significantly higher than the IC50 of TAT in either K-12 strain (Table 5). Although the IC50 values of DB4-162 in both K-12 strains are high, it is worth noting that DB4-162 is more active against the +Bla K-12 *E. coli* strain that is producing β-lactamase considering that ampicillin is unable to kill this strain at low millimolar concentrations.

The effect of copper on the IC50 of DB4-162 was also assessed in order to test its possible influence on activity. The addition of 10 μM copper to the test media did not significantly change the IC50 of DB4-162 in the +Bla K-12 strain of E. coli, but in the −Bla strain the IC50 of DB4-162 decreases from 227 to 39 µM which is roughly the same IC50 of TAT in the −Bla strain when copper is added to the media. However, the removal of copper from the media via BCS increased the IC50 of DB4-162 in −Bla K-12 from 39 to 54 µM. Likewise, in media containing 500 µM BCS the IC50 of DB4-162 in +Bla K-12 increased from 147 to 179 µM.

5.5.6. Testing DB4-162 in UTI89 *Escherichia coli*

UTI89 *E. coli* is susceptible to ampicillin and we calculated the IC50 of ampicillin to be 3 µM. However, resistant strains of UTI89 *E. coli* can cause persistent urinary tract infections. The resistant mutant strain was produced by transfecting UTI89 with the pCOM plasmid that encodes for a TEM-1 β-lactamase. DB4-162 has an IC50 of 93 µM in UTI89 which is only slightly under the 100 µM active/inactive threshold. Similarly, the IC50 of DB4-162 is 112 µM in the pCOM mutant that produces β-lactamase. These IC50 values indicate that DB4-162 is not especially active in UTI89/pCOM *E. coli*. This is surprising given the low-µM IC50 values of TAT in both strains (Table 4). However, it should be noted that, in the pCOM strain, the prochelator is still more active than ampicillin (Table 4).

The inclusion of supplemental copper slightly increases the IC50 of DB4-162 in UTI89 from 93 to 97 µM. However, with a P value of 0.70, these two values are not statistically different. When BCS is included in the media the IC50 of DB4-162 in UTI89 decreases from 93 to 77 µM. However, the effects of BCS are not significantly significant either (P=0.15). The IC50 of DB4-162 in the pCOM mutant strain decreases from 112 to 93 µM upon the inclusion of additional copper, but this decrease is statistically insignificant (P=0.99). Conversely, the IC50 of DB4-162 in the ampicillin-resistant pCOM strain increases from 93 to 168 µM. The observation that the IC50 values of DB4-162 in the UTI89 and pCOM *E. coli* strains do not change when copper is added to the media does not support a copper-dependent mechanism of action for DB4-162. Only in pCOM *E. coli* does the IC50 of DB4-162 increase when BCS is added to the media.

5.5.7. Testing DB4-162 in ESBL *Escherichia coli*

*E. coli* that produce extended-spectrum β-lactamases are highly resistant to many penicillin and cephalosporin antibiotics. In fact, the IC50 of ampicillin in ESBL *E. coli* is greater than 250 µM. Through broth microdilution, the prochelator DB4-162 was found to have an IC50 value of 22 µM in ESBL *E. coli*. This value is 90% lower than the IC50 of DB4-162 in the ampicillin-susceptible −Bla K-12 *E. coli* strain (FIG. 12). It is interesting that DB4-162 is more active against ESBL *E. coli* than it is against −Bla K-12 *E. coli* considering that the IC50 of TAT is 41 µM in ESBL *E. coli* and 23 µM in −Bla *E. coli* (Table 5).

The activity of DB4-162 in media supplemented with copper or BCS was also evaluated. The IC50 of DB4-162 in ESBL *E. coli* does not decrease significantly from 22 µM in the presence of 10 µM supplemental copper. However, the addition of BCS to the media caused the IC50 of DB4-162 in ESBL *E. coli* to more than double from 22 to 50 µM. Taken together, the IC50 responses to copper and BCS do not clearly indicate a copper-dependent mechanism of action for DB4-162 in ESBL *E. coli*.

5.5.8. Testing DB4-162 in *Klebsiella pneumoniae*

*K. pneumoniae* can produce a number of β-lactamases that confer upon the strain resistance to a broad-spectrum of clinical antibiotics. [47] A strain of ampicillin-resistant Klebs was screened against ampicillin and DB4-162. In Klebs, the IC50 of ampicillin is greater than 250 µM and the IC50 of DB4-162 was found to be 28 µM (FIG. 12) which is very similar to the IC50 of TAT in the same Klebs strain (Table 5).

When DB4-162 is evaluated against Klebs in the presence of supplemental copper, the IC50 slightly decreased from 28 µM to 22 µM. Including BCS in the growth media caused a similar decrease in the IC50 of DB4-162 from 28 to 24 µM. However, neither the decrease with copper (P=0.44) nor the decrease with BCS (P=0.61) are statistically significant. These observations do not indicate a copper-dependence on the activity of DB4-162 in *Klebsiella pneumoniae*.

5.5.9. Testing DB4-162 in *Staphylococcus aureus*

Figure 13:
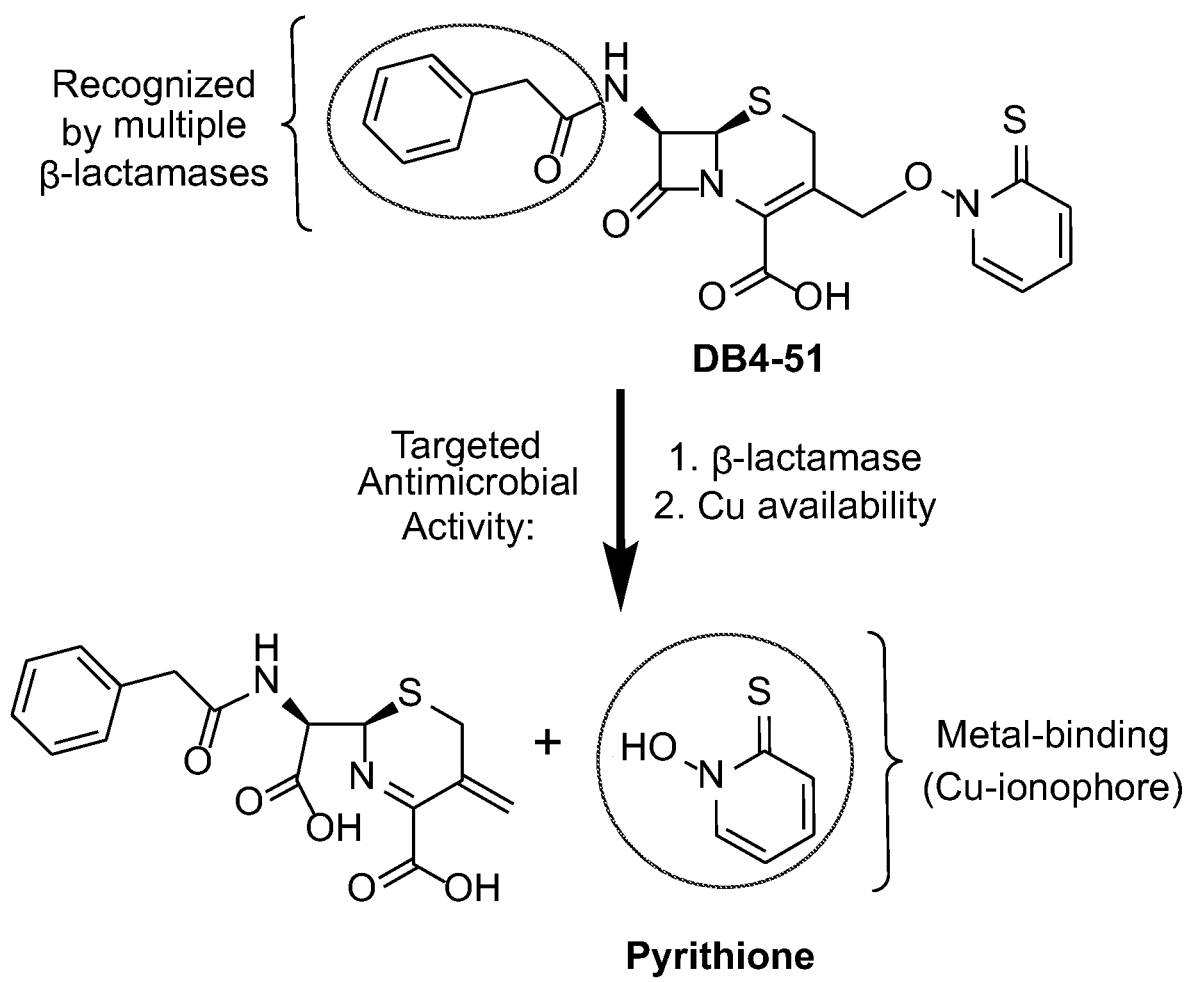
FIG. 13: shows the prochelator approach to selectively target drug-resistant bacteria. Prochelator DB4-51 releases a metal-binding antimicrobial agent in the presence of drug-resistant bacteria that produce β-lactamase enzymes. The metal-binding agent synergizes with bioavailable copper to exacerbate microbial killing.

MRSA is well-positioned to cause opportunistic infections in patients with compromised immune systems. It should be noted that *Staph. aureus* is gram-positive and, lacking a secondary membrane, primarily expresses β-lactamase into the extracellular space.[48, 49] MRSA is difficult to treat due to its resistance to a variety of β-lactam antibiotics. For example, the IC50 of ampicillin is greater than 250 µM in the USA300 MRSA strain used here. When DB4-162 was screened against MRSA the IC50 was found to be 2.4 µM (FIG. 13). The IC50 of TAT in MRSA was calculated and is reported to be 23 µM (Table 5).

When 10 µM supplemental copper was added to the growth media, the IC50 of DB4-162 increased slightly from 2.4 to 2.7 µM. However, with a P value of 0.19, this change is statistically insignificant. Likewise, there is no change in the IC50 of DB4-162 in MRSA when BCS is added to the media. These observations suggest there is no correlation between the antibacterial activity of DB4-162 in MRSA and the presence of copper in the media.

TABLE 4

| | IC50 values of DB4-162 and ampicillin in select bacteria. IC50 (µM) | | | |
|---|---|---|---|---|
| Bacteria | DB4-162 | DB4-162 + Cu | DB4-162 + BCS | Ampicillin |
| −Bla K-12 *E. coli* | 227 (204.7-252.3) | 39 (33.8-43.9) | 54 (40.0-73.3) | 8 (7.2-8.9) |
| +Bla K-12 *E. coli* | 143 (114.1-178.0) | 147 (130.6-166.1) | 179 (137.0-233.1) | >250 |
| UTI89 *E. coli* | 93 (66.9-128.9) | 97 (86.2-108.6) | 77 (67.1-88.9) | 3 (1.8-4.5) |
| pCOM *E. coli* | 112 (62.3-180.7) | 93 (81.8-106.6) | 168 (126.0-222.9) | >250 |

TABLE 4-continued

IC50 values of DB4-162 and ampicillin in select bacteria. IC50 (µM)

| Bacteria | DB4-162 | DB4-162 + Cu | DB4-162 + BCS | Ampicillin |
|---|---|---|---|---|
| ESBL E. coli | 22 (20.0-23.3) | 21 (20.4-22.3) | 50 (45.7-55.3) | >250 |
| MRSA | 2.4 (2.1-2.9) | 2.7 (2.6-2.8) | 2.4 (2.2-3.2) | >250 |
| Klebs | 28 (25.4-30.7) | 22 (14.5-33.7) | 24 (16.5-35.6) | >250 |

IC50 values were calculated via broth microdilution of DB4-162 in LB broth, LB supplemented with 10 µM $CuCl_2$, or LB supplemented with 500 µM BCS. IC50 values for ampicillin were calculated via broth microdilution in LB broth only. Values are listed as the mean followed by the 95% confidence interval about the mean. Mean and confidence intervals were calculated from a variable slope, non-linear regression fit to the dose-response $OD_{600}$ data.

TABLE 5

IC50 values of TAT and ampicillin in pathogenic bacteria. bacteria. IC50 (µM)

| Bacteria | TAT | TAT + Cu | TAT + BCS | Ampicillin |
|---|---|---|---|---|
| −Bla K-12 E. coli | 23 (16.5-32.7) | 36 (19.3-65.3) | 70 (57.5-84.0) | 8 (7.2-8.9) |
| +Bla K-12 E. coli | 36 (32.5-40.0) | 38 (25.7-56.0) | 70 (46.6-103.6) | >250 |
| UTI89 E. coli | 6 (3.2-10.1) | 9 (7.3-11.5) | 38 (18.2-77.1) | 3 (1.8-4.5) |
| pCOM E. coli | 6 (4.2-9.3) | 7 (5.5-8.3) | 28 (24.4-33.0) | >250 |
| ESBL E. coli | 41 (37.5-45.2) | — | — | >250 |
| MRSA | 23 (15.1-35.2) | 10 (1.8-54.4) | 29 (24.9-32.9) | >250 |
| Klebs | 14 (9.0-22.1) | 26 (10.3-41.3) | 51 (44.5-58.1) | >250 |

$IC_{50}$ values were calculated via broth microdilution of TAT in LB broth, LB containing 10 µM $CuCl_2$, or LB containing 500 µM BCS. Values are listed as the mean followed by the 95% confidence interval about the mean. $IC_{50}$ values were calculated from a variable slope, nonlinear regression fit to the dose-response OD600 data.

5.5.10. Cytotoxicity of DB4-162 and TAT in Mammalian Cells

The toxicity of DB4-162 and TAT were evaluated in mammalian cells using the CellTox Green Cytotoxicity fluorescence assay. The following cell lines were utilized: CCD-19Lu human lung fibroblast cells and HepG2 human liver epithelial cells. Using the CellTox Green Cytotoxicity assay, the viability of mammalian cells was monitored as a function of their membrane stability. The assay contains a membrane-impermeable dye that binds DNA with a fluorescence turn-on. This dye allows the visualization of cell lysis as a proportional fluorescence increase. The resulting fluorescence intensities were normalized using negative (media) and positive (a lethal dose of 1% Triton-X) controls. The assay manufacturers recommend that the fluorescence be recorded after a 0-24 hour incubation period.

This invention discloses an innovative method of turning bacterial resistance into a drug target that works in synergy with the altered metal status associated with infection. By conditionally activating chelators in the niche of bacterial infection the compounds described above can exert their antibiotic effects on the basis of metallobiology. To that end, we have described the synthesis of a β-lactamase-activated prochelator and its stability in aqueous environments as well as its conversion in the presence of a commercially available β-lactamase. Using fluorescence assays we have demonstrated the ability of DB4-51 and DB4-162, upon activation, to bind Cu2+ and Zn2+. Finally, we have Illustrated the antibiotic properties of DB4-51 and DB4-162 against the K-12 E coli in relation to known antibiotics and demonstrated the potential for modification of the backbone to elicit the targeted release of various metal chelators.

6. REFERENCES

1. Powers, J. H., Anti-microbial drug development—the past, the present, and the future. *Clinical Microbiology & Infection* 2004, 70, 23.
2. Coates, A. R. M.; Halls, G.; Hu, Y., Novel classes of antibiotics or more of the same? *British Journal of Pharmacology* 2011, 163, 184.
3. Clatworthy, A. E.; Pierson, E.; Hung, D. T., Targeting virulence: A new paradigm for antimicrobial therapy. *Nat Chem Biol* 2007, 3, 541.
4. Cho, H.; Uehara, T.; Bernhardt, Thomas G., Beta-lactam antibiotics induce a lethal malfunctioning of the bacterial cell wall synthesis machinery. *Cell* 2014, 159, 1300.
5. Boucher, H. W.; Talbot, G. H.; Benjamin, D K; Bradley, J.; Guidos, R. J.; Jones, R. N.; Murray, B. E.; Bonomo, R A; Gilbert, D.; America, f.t.l.D.S.o. 10×'20 progress-development of new drugs active against gram-negative bacilli: An update from the infectious diseases society of America. *Clinical Infectious Diseases* 2013, 56, 1685.
6. Kim, S.; Lieberman, T. D.; Kishony, R., Alternating antibiotic treatments constrain evolutionary paths to multidrug resistance. *Proceedings of the National Academy of Sciences* 2014, 111, 14494.
7. Tamma, P. O.; Cosgrove, S. E.; Maragakis, L. L., Combination therapy for treatment of infections with gram-negative bacteria. *Clinical Microbiology Reviews* 2012, 25, 450.

8. Qiu, D.-H.; Huang, Z.-L.; Zhou, T.; Shen, C.; Hider, R. C., In vitro inhibition of bacterial growth by iron chelators. 2011, 314, 107.
9. Dinning; Adham, A. L.; Austin; Charlton; Collier, Pyrithione biocide interactions with bacterial phospholipid head groups. *Journal of Applied Microbiology* 1998, 85, 132.
10. Lemire, J. A.; Harrison, J. J.; Turner, R. J., Antimicrobial activity of metals: Mechanisms, molecular targets and applications. *Nat Rev Micro* 2013, 11, 371.
11. Grenier, D.; Huot, M.-P.; Mayrand, D., Iron-chelating activity of tetracyclines and its impact on the susceptibility of *actinobacillus* actinomycetemcomitansto these antibiotics. *Antimicrobial Agents and Chemotherapy* 2000, 44, 763.
12. Albert, A.; Rubbo, S. D.; Goldacre, R. J.; Balfour, B. G., The influence of chemical constitution on antibacterial activity. Part iii: A study of 8-hydroxyquinoline (oxine) and related compounds. *British Journal of Experimental Pathology* 1947, 28, 69.
13. Kielar, F.; Wang, Q.; Boyle, P. O.; Franz, K. J., A boronate prochelator built on a triazole framework for peroxide-triggered tridentate metal binding. *Inorganica Chimica Acta* 2012, 393, 294.
14. Kielar, F.; Helsel, M. E.; Wang, Q.; Franz, K. J., Prochelator bhapi protects cells against paraquat-induced damage by res-triggered iron chelation. *Metallomics* 2012, 4, 899.
15. Foye, W. O., Role of metal-binding in the biological activities of drugs. *Journal of Pharmaceutical Sciences* 1961, 50, 93.
16. Black, J. G.; Howes, D., Toxicity of pyrithiones. *Clinical Toxicology* 1978, 13, 1.
17. Page, M.1.; Proctor, P., Mechanism of β-lactam ring opening in cephalosporins. *Journal of the American Chemical Society* 1984, 106, 3820.
18. Phelan, R. M.; Ostermeier, M.; Townsend, C. A. Design and synthesis of a Plactamase activated 5-fluorouracil prodrug. *Bioorganic & Medicinal Chemistry Letters* 2009, 19, 1261.
19. Gao, W.; Xing, B.; Tsien, R. Y.; Rao, J., Novel fluorogenic substrates for imaging β-lactamase gene expression. *Journal of the American Chemical Society* 2003, 125, 11146.
20. van Berkel, S. S.; Brem, J.; Rydzik, A. M.; Salimraj, R.; Cain, R.; Verma, A.; Owens, R. J.; Fishwick, C. W. G.; Spencer, J.; Schofield, C. J., Assay platform for clinically relevant metallo-β-lactamases. *Journal of Medicinal Chemistry* 2013, 56, 6945.
21. O'Callaghan, C. H.; Sykes, R. B.; Staniforth, S. E., A new cephalosporin with a dual mode of action. *Antimicrobial Agents and Chemotherapy* 1976, 10, 245.
22. Ochiai et al., Cephalosporin derivatives. U.S. Pat. No. 3,890,309, 1975.
23. Festa, Richard A.; Helsel, Marian E.; Franz, Katherine J.; Thiele, Dennis J., Exploiting innate immune cell activation of a copper-dependent antimicrobial agent during infection. *Chemistry & Biology* 2014, 21, 977.
24. Reeder, N. L.; Kaplan, J.; Xu, J.; Youngquist, R. S.; Wallace, J.; Hu, P.; Juhlin, K. D.; Schwartz, J. R.; Grant, R. A.; Fiene, A.; Nemeth, S.; Reichling, T.; Tiesman, J. P.; Mills, T.; Steinke, M.; Wang, S. L.; Saunders, C. W., Zinc pyrithione inhibits yeast growth through copper influx and inactivation of iron-sulfur proteins. *Antimicrob. Agents Chemother.* 2011 1 55, 5753.
25. Schlesinger, S. R.; Bruner, B.; Farmer, P. J.; Kim, S.-K., Kinetic characterization of a slow-binding inhibitor of bla2: Thiomaltol. *Journal of Enzyme Inhibition & Medicinal Chemistry* 2013, 28, 137.
26. Boyer, H. W., and Roulland-dussoix, D. (1969) A complementation analysis of the restriction and modification of DNA in *Escherichia coli, J. Mol. Biol.* 41, 459-472.
27. Mulvey, M. A., Lopez-Boado, Y. S., Wilson, C. L., Roth, R., Parks, W. C., Heuser, J., and Hultgren, S. J. (1998) Induction and evasion of host defenses by type 1-piliated uropathogenic *Escherichia coli, Science* 282, 1494-1497.
28. Valdivia, R. H., Hromockyj, A. E., Monack, D., Ramakrishnan, L., and Falkow, S. (1996) Applications for green fluorescent protein (gfp) in the study of hostpathogen interactions, *Gene* 173, 47-52.
29. Bae, I.-G., Tonthat, G. T., Stryjewski, M. E., Rude, T. H., Reilly, L. F., Barriere, S. L., Genter, F. C., Corey, G. R., and Fowler, V. G. (2009) Presence of genes encoding the panton-valentine leukocidin exotoxin is not the primary determinant of outcome in patients with complicated skin and skin structure infections due to methicillin-resistant *Staphylococcus aureus*: Results of a multinational trial, *J. Clin. Microbiol.* 47, 3952-3957.
30. Shirahata, K.; Deguchi, T.; Hayashi, T.; Matsubara, I.; Suzuki, T., THE STRUCTURES OF FLUOPSINS C AND F. *The Journal of Antibiotics* 1970, 23 (11), 546-550.
31. Reeder, N. L.; Xu, J.; Youngquist, R. S.; Schwartz, J. R.; Rust, R. C.; Saunders, C. W., The antifungal mechanism of action of zinc pyrithione. *Br J Dermatol* 2011, 165 Suppl 2, 9-12.
32. Bond, A. D.; Jones, W., Divalent complexes of 3-hydroxy-4-methyl-2(3H)-thiazolethione with Co—Zn: synthesis, X-ray crystal structures and the structure-directing influence of C—H[three dots, centered]S interactions. *Journal of the Chemical Society, Dalton Transactions* 2001, (20), 3045-3051.
33. Bond, A. D.; Jones, W., Solid-state study of cyclic thiohydroxamic acids: 1-hydroxy-2(1H)-pyridinethione and 3-hydroxy-4-methyl-2(3H)-thiazolethione. *Journal of Physical Organic Chemistry* 2000, 13 (7), 395-404.
34. Bond, A. D.; Jones, W., Synthesis and X-ray crystal structures of bis(3-hydroxy-4-methyl-2(3H)-thiazolethiolato-S 2,O)bis(dimethylsulfoxide-O)M, M=cobalt(II) and nickel(II). *Transition Metal Chemistry* 27 (4), 407-410.
35. Bush, K.; Macalintal, C.; Rasmussen, B. A.; Lee, V. J.; Yang, Y., Kinetic interactions of tazobactam with beta-lactamases from all major structural classes. *Antimicrobial Agents and Chemotherapy* 1993, 37 (4), 851-858.
36. Faridoon; Hussein, W. M.; Vella, P.; Islam, N. U.; Ollis, D. L.; Schenk, G.; McGeary, R. P., 3-Mercapto-1,2,4-triazoles and N-acylated thiosemicarbazides as metallo-β-lactamase inhibitors. *Bioorganic & Medicinal Chemistry Letters* 2012, 22 (1), 380-386.
37. Kurosaki, H.; Yamaguchi, Y.; Higashi, T.; Soga, K.; Matsueda, S.; Yumoto, H.; Misumi, S.; Yamagata, Y.; Arakawa, Y.; Goto, M., Irreversible Inhibition of Metallo-β-lactamase (IMP-1) by 3-(3-Mercaptopropionylsulfanyl) propionic Acid Pentafluorophenyl Ester. *Angewandte Chemie International Edition* 2005, 44 (25), 3861-3864.
38. Bush, K., Beta-lactamase inhibitors from laboratory to clinic. *Clinical Microbiology Reviews* 1988, 1 (1), 109-123.
39. Reeder, N. L., Kaplan, J., Xu, J., Youngquist, R. S., Wallace, J., Hu, P., Juhlin, K. D., Schwartz, J. R., Grant, R. A., Fiene, A., Nemeth, S., Reichling, T., Tiesman, J. P., Mills, T., Steinke, M., Wang, S. L., and Saunders, C. W. (2011) Zinc pyrithione inhibits yeast growth through copper influx and inactivation of iron-sulfur proteins, *Antimicrob. Agents Chemother.* 55, 5753-5760.
40. Yasokawa, D., Murata, S., Iwahashi, Y., Kitagawa, E., Kishi, K., Okumura, Y., and Iwahashi, H. (2010) DNA microarray analysis suggests that zinc pyrithione causes iron starvation to the yeast *Saccharomyces cerevisiae, J. Biosci. Bioeng.* 109, 479-486.
41. Kershaw, C. J., Brown, N. L., Constantinidou, C., Patel, M. D., and Hobman, J. L. (2005) The expression profile of *Escherichia coli* k-12 in response to minimal, optimal and excess copper concentrations, *Microbiology* 151, 1187-1198.
42. Hernández-Montes, G., Argüello, J. M., and Valderrama, B. (2012) Evolution and diversity of periplasmic proteins involved in copper homeostasis in gamma proteobacteria, *BMC Microbiol.* 12, 1-14.
43. Djoko, K. Y., Ong, C.-1. Y., Walker, M. J., and McEwan, A. G. (2015) The role of copper and zinc toxicity in innate immune defense against bacterial pathogens, *J. Biol. Chem.* 290, 18954-18961.
44. Spyker, D. A.; Thomas, B. L.; Sande, M. A.; Bolton, W. K., Pharmacokinetics of Cefaclor and Cephalexin: Dosage Nomograms for Impaired Renal Function. *Antimicrobial Agents and Chemotherapy* 1978, 14 (2), 172-177.
45. Christ, W., Pharmacological properties of cephalosporins. *Infection* 1991, 19 (5), S244-S252.
46. Massidda, O.; Mingoia, M.; Fadda, D.; Whalen, M. B.; Montanari, M. P.; Varaldo, P. E., Analysis of the β-lactamase plasmid of borderline methicillin-susceptible *Staphylococcus aureus*: Focus on bla complex genes and cadmium resistance determinants cadD and cadX. *Plasmid* 2006, 55 (2), 114-127.
47. Hirsch, E. B.; Tam, V. H., Detection and treatment options for *Klebsiella pneumoniae* carbapenemases (KPCs): an emerging cause of multidrug-resistant infection. *Journal of Antimicrobial Chemotherapy* 2010, 65 (6), 1119-1125.
48. Kernodle, D. S.; McGraw, P. A.; Stratton, C. W.; Kaiser, A. B., Use of extracts versus whole-cell bacterial suspensions in the identification of *Staphylococcus aureus* beta-lactamase variants. *Antimicrobial Agents and Chemotherapy* 1990, 34 (3), 420-425.
49. Deák, E.; SzabóA, I.; Kálmáczhelyi, A.; Gál, Z.; Barabás, G.; Penyige, A., Membrane-bound and extracellular β-lactamase production with developmental regulation in *Streptomyces griseus* NRRL B-2682. *Microbiology* 1998, 144 (8), 2169-2177.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. An antibacterial prochelator that targets antibiotic resistant bacteria having the following formula:

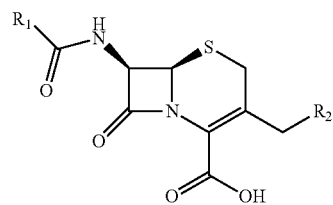

wherein $R_1$ is selected from the group consisting of:

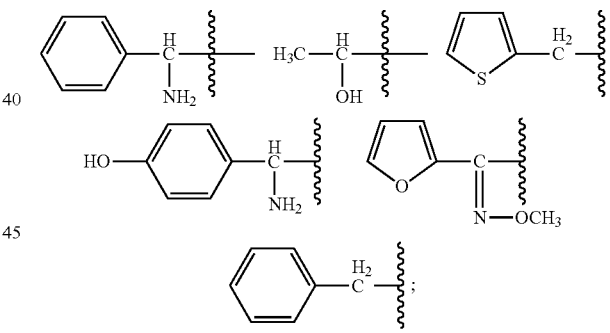

$R_2$ is

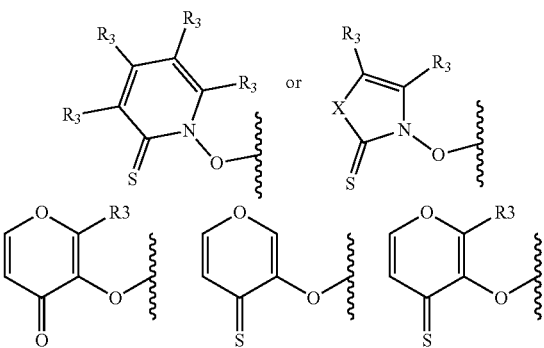

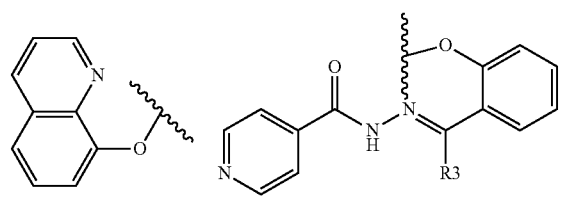

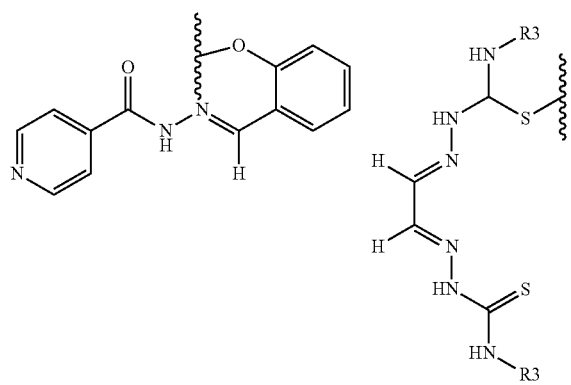

wherein each $R_3$ is alkyl, aryl, H, OH, $NH_2$, SH or two adjacent $R_3$ may form a bicyclic moiety with a 5 or 6-member aromatic ring;

X is N-alkyl, NH, O or S; and any salt thereof.

2. The antibacterial prochelator of claim 1, wherein $R_1$ is

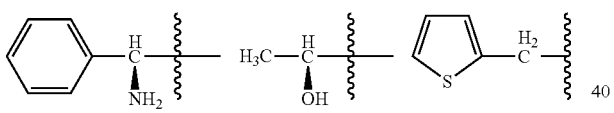

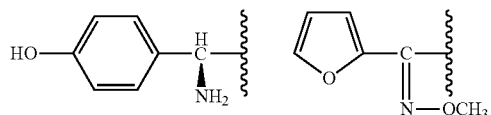

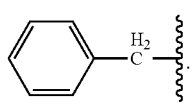

3. The antibacterial prochelator of claim 1, wherein $R_2$ is

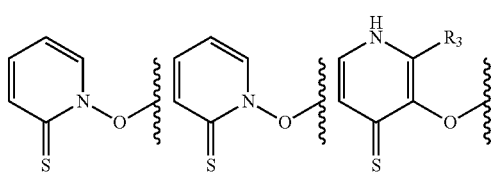

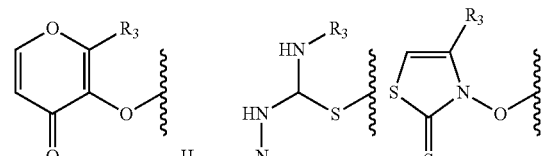

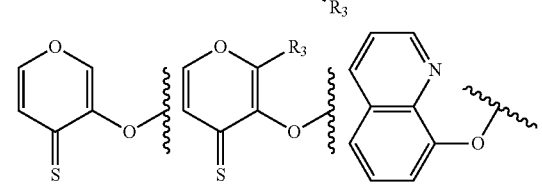

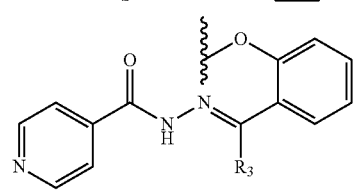

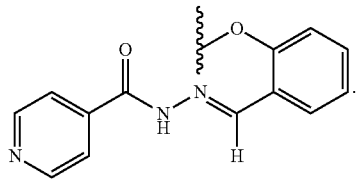

4. The antibacterial prochelator of claim 3, wherein $R_2$ is

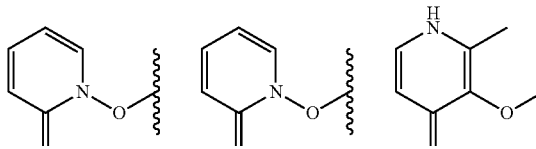

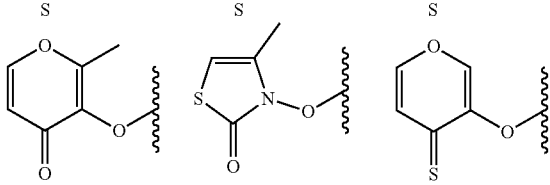

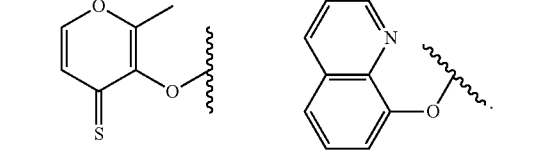

5. The antibacterial prochelator of claim 1 wherein the antibacterial prochelator is 2-((((6R,7R)-2-carboxy-8-oxo-7-(2-phenylacetamido)-5-thia-1-azabicyclo[4.2.0]oct-2-en-3-yl)methyl)thio)pyridine 1-oxide.

6. The antibacterial prochelator of claim 1 wherein the antibacterial prochelator is (6R,7R)-3-(((4-methyl-2-thioxothiazol-3(2H)-yl)oxy)methyl)-8-oxo-7-(2-phenylacetamido)-5-thia-1-azabicyclo[4.2.0]oct-2-ene-2-carboxylic acid.

7. A pharmaceutical composition comprising the antibacterial prochelator of claim 1 and a pharmaceutically acceptable carrier.

8. A pharmaceutical composition comprising the antibacterial prochelator of claim 1 and a metal salt.

9. The pharmaceutical composition of claim 8, wherein the metal salt is a copper, iron or zinc salt.

* * * * *